US009645179B2

United States Patent
White et al.

(10) Patent No.: US 9,645,179 B2
(45) Date of Patent: *May 9, 2017

(54) SELF-TEST FOR ANALGESIC PRODUCT

(71) Applicants: Incline Therapeutics, Inc., Redwood City, CA (US); Alza Corporation, Vacaville, CA (US)

(72) Inventors: Bradley E. White, Lebanon, OH (US); John Lemke, Pleasanton, CA (US); Paul Hayter, Mountain View, CA (US); Corinna X. Chen, Oakland, CA (US); Brian W. Read, Brier, WA (US); Jason E. Dougherty, Seattle, WA (US)

(73) Assignees: Incline Therapeutics, Inc., Redwood City, CA (US); Alza Corporation, Vacaville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/815,676

(22) Filed: Jul. 31, 2015

(65) Prior Publication Data
US 2015/0338445 A1  Nov. 26, 2015

Related U.S. Application Data

(60) Continuation of application No. 13/866,371, filed on Apr. 19, 2013, now Pat. No. 9,095,706, which is a (Continued)

(51) Int. Cl.
*A61N 1/30* (2006.01)
*G01R 19/145* (2006.01)
(Continued)

(52) U.S. Cl.
CPC ......... *G01R 19/145* (2013.01); *A61N 1/0416* (2013.01); *A61N 1/0432* (2013.01);
(Continued)

(58) Field of Classification Search
CPC .......... A61N 1/18; A61N 1/303; A61N 1/325; A61N 1/36128; A61N 1/3615; A61M 5/172
See application file for complete search history.

(56) References Cited

U.S. PATENT DOCUMENTS

| 4,141,359 A | 2/1979 | Jacobsen et al. |
| 4,474,570 A | 10/1984 | Ariura et al. |

(Continued)

FOREIGN PATENT DOCUMENTS

| CN | 1099300 C | 1/2003 |
| CN | 1972681 A | 5/2007 |

(Continued)

OTHER PUBLICATIONS

Ahmad et al.; Fentanyl HCl iontophoretic transdermal system versus intravenous morphine pump after gynecologic surgery; Arch Gynecol Obstet; vol. 276, No. 3; pp. 251-258; Sep. 2007.

(Continued)

*Primary Examiner* — Deanna K Hall
(74) *Attorney, Agent, or Firm* — Shay Glenn LLP

(57) ABSTRACT

Electrotransport drug delivery devices, system and methods of using configured to determine if a current is present between the anode and cathode when drug is not intended to be delivered by the device. These devices/systems may include an off-current module to determine that any current (e.g., which may be inferred by measuring potential difference between the anode and cathode of the device) flowing between the anode and cathode is below a threshold value when the device is not supposed to be delivering drug, thereby preventing unintended delivery of drug and/or alerting a user that unintended delivery of drug may occur.

23 Claims, 24 Drawing Sheets

Related U.S. Application Data division of application No. 13/476,960, filed on May 21, 2012, now Pat. No. 8,428,708.

(51) Int. Cl.

| | | |
|---|---|---|
| *A61N 1/08* | (2006.01) | |
| *G01R 19/165* | (2006.01) | |
| *G08B 21/18* | (2006.01) | |
| *A61N 1/18* | (2006.01) | |
| *A61N 1/32* | (2006.01) | |
| *A61N 1/04* | (2006.01) | |

(52) U.S. Cl.
CPC .............. *A61N 1/08* (2013.01); *A61N 1/18* (2013.01); *A61N 1/303* (2013.01); *A61N 1/325* (2013.01); *A61N 1/327* (2013.01); *G01R 19/165* (2013.01); *G08B 21/182* (2013.01)

(56) References Cited

U.S. PATENT DOCUMENTS

| | | | |
|---|---|---|---|
| 4,588,580 A | 5/1986 | Gale et al. | |
| 4,698,582 A | 10/1987 | Braun et al. | |
| 4,731,926 A | 3/1988 | Sibalis | |
| 4,752,285 A | 6/1988 | Petelenz et al. | |
| 4,822,802 A | 4/1989 | Levy et al. | |
| 4,878,892 A | 11/1989 | Sibalis et al. | |
| 4,931,046 A | 6/1990 | Newman | |
| 5,006,108 A | 4/1991 | LaPrade | |
| 5,019,034 A | 5/1991 | Weaver et al. | |
| 5,047,007 A | 9/1991 | McNichols et al. | |
| 5,057,072 A | 10/1991 | Phipps | |
| 5,084,008 A | 1/1992 | Phipps | |
| 5,135,477 A | 8/1992 | Untereker et al. | |
| 5,135,479 A | 8/1992 | Sibalis et al. | |
| 5,147,297 A | 9/1992 | Myers et al. | |
| 5,199,155 A | 4/1993 | Cord et al. | |
| 5,203,768 A | 4/1993 | Haak et al. | |
| 5,224,927 A | 7/1993 | Tapper | |
| 5,224,928 A | 7/1993 | Sibalis et al. | |
| 5,232,438 A | 8/1993 | Theeuwes et al. | |
| 5,232,448 A | 8/1993 | Zdeb | |
| 5,246,418 A | 9/1993 | Haynes et al. | |
| 5,254,081 A | 10/1993 | Maurer et al. | |
| 5,306,235 A | 4/1994 | Haynes | |
| 5,314,502 A | 5/1994 | McNichols et al. | |
| H1324 H | 6/1994 | Dalke et al. | |
| 5,320,597 A | 6/1994 | Sage, Jr. et al. | |
| 5,358,483 A | 10/1994 | Sibalis | |
| D352,357 S | 11/1994 | Ashley | |
| 5,445,609 A | 8/1995 | Lattin et al. | |
| 5,458,569 A | 10/1995 | Kirk, III et al. | |
| D372,098 S | 7/1996 | Lattin et al. | |
| 5,551,953 A | 9/1996 | Lattin et al. | |
| 5,562,607 A | 10/1996 | Gyory | |
| 5,603,693 A | 2/1997 | Frenkel et al. | |
| 5,644,463 A | 7/1997 | El-Sharkawi et al. | |
| D384,745 S | 10/1997 | Lattin et al. | |
| 5,688,232 A | 11/1997 | Flower | |
| 5,697,896 A | 12/1997 | McNichols et al. | |
| 5,718,562 A | 2/1998 | Lawless et al. | |
| 5,804,957 A | 9/1998 | Coln | |
| 5,843,014 A | 12/1998 | Lattin et al. | |
| 5,879,143 A | 3/1999 | Cote et al. | |
| 5,919,155 A | 7/1999 | Lattin et al. | |
| 5,928,196 A | 7/1999 | Johnson et al. | |
| 5,983,133 A | 11/1999 | Garde et al. | |
| 6,029,083 A | 2/2000 | Flower et al. | |
| 6,035,234 A | 3/2000 | Riddle et al. | |
| 6,039,977 A | 3/2000 | Venkatraman et al. | |
| 6,047,208 A | 4/2000 | Flower | |
| 6,049,733 A | 4/2000 | Phipps et al. | |
| 6,086,572 A | 7/2000 | Johnson et al. | |
| 6,167,302 A | 12/2000 | Millot | |
| 6,171,294 B1 | 1/2001 | Southam et al. | |
| 6,181,963 B1 | 1/2001 | Chin et al. | |
| 6,216,033 B1 | 4/2001 | Southam et al. | |
| 6,295,469 B1 | 9/2001 | Linkwitz et al. | |
| 6,355,025 B1 | 3/2002 | Phipps et al. | |
| 6,385,488 B1 | 5/2002 | Flower et al. | |
| 6,425,892 B2 | 7/2002 | Southam et al. | |
| 6,453,195 B1 | 9/2002 | Thompson | |
| 6,881,208 B1 | 4/2005 | Phipps et al. | |
| 6,949,081 B1 | 9/2005 | Chance | |
| 6,970,739 B1 | 11/2005 | Inoue | |
| 6,975,902 B2 | 12/2005 | Phipps et al. | |
| 7,016,724 B2 | 3/2006 | Henley et al. | |
| 7,027,859 B1 | 4/2006 | McNichols et al. | |
| 7,302,293 B2 | 11/2007 | Southam et al. | |
| 7,597,679 B2 | 10/2009 | Jespersen et al. | |
| 7,621,893 B2 | 11/2009 | Moberg et al. | |
| 7,660,627 B2 | 2/2010 | McNichols et al. | |
| 7,766,873 B2 | 8/2010 | Moberg et al. | |
| 7,844,326 B2 | 11/2010 | Dent et al. | |
| 8,301,238 B2 | 10/2012 | Netzel et al. | |
| 8,428,708 B1 * | 4/2013 | White ................... A61N 1/303 604/20 |
| 8,428,709 B1 | 4/2013 | White et al. | |
| 9,095,706 B2 * | 8/2015 | White ................... A61N 1/303 | |
| 2002/0128591 A1 | 9/2002 | Kleiner et al. | |
| 2002/0165481 A1 | 11/2002 | Hofmann et al. | |
| 2002/0183702 A1 | 12/2002 | Henley et al. | |
| 2002/0198504 A1 | 12/2002 | Risk et al. | |
| 2003/0191946 A1 | 10/2003 | Auer et al. | |
| 2004/0085215 A1 | 5/2004 | Moberg et al. | |
| 2005/0004506 A1 | 1/2005 | Gyory | |
| 2006/0025715 A1 | 2/2006 | Henley et al. | |
| 2006/0161827 A1 | 7/2006 | Gohel et al. | |
| 2007/0035903 A1 | 2/2007 | Sullivan et al. | |
| 2008/0234627 A1 | 9/2008 | Dent et al. | |
| 2008/0234628 A1 | 9/2008 | Dent et al. | |
| 2009/0043244 A1 | 2/2009 | Inan | |
| 2009/0171502 A1 | 7/2009 | Freidin | |
| 2010/0037680 A1 | 2/2010 | Moberg et al. | |
| 2012/0253262 A1 | 10/2012 | Lemke et al. | |
| 2015/0196754 A1 | 7/2015 | White et al. | |

FOREIGN PATENT DOCUMENTS

| | | |
|---|---|---|
| CN | 102421480 | 4/2012 |
| EP | 1084729 A2 | 3/2001 |
| EP | 1532995 | 5/2005 |
| GB | 2239803 A | 7/1991 |
| JP | H04-208166 A | 7/1992 |
| JP | H05-004482 U | 1/1993 |
| JP | 05508558 A | 12/1993 |
| JP | H06-62433 U | 9/1994 |
| JP | 07-067971 | 3/1995 |
| JP | 07-124265 | 5/1995 |
| JP | 11-128369 A | 5/1999 |
| JP | H11-505445 A | 5/1999 |
| JP | 2000157320 | 6/2000 |
| JP | 2001120669 A | 5/2001 |
| JP | 2003260144 A | 9/2003 |
| KR | 97000259 B1 | 3/1997 |
| NZ | 541949 A | 11/2008 |
| RU | 223608 C2 | 7/2004 |
| RU | 2269368 C1 | 2/2006 |
| WO | WO 90/03825 A1 | 4/1990 |
| WO | WO 91/15257 A1 | 10/1991 |
| WO | WO 91/15258 A1 | 10/1991 |
| WO | WO 93/01807 A1 | 2/1993 |
| WO | WO 95/27530 A1 | 10/1995 |
| WO | WO 96/36394 A1 | 11/1996 |
| WO | WO 97/07854 A1 | 3/1997 |
| WO | WO 99/30773 A1 | 6/1999 |
| WO | WO 01/41863 A1 | 6/2001 |
| WO | WO 2006/077262 A1 | 7/2006 |

(56) References Cited

FOREIGN PATENT DOCUMENTS

WO     WO 2009/120840 A2    10/2009
WO     WO 2010/078313 A1     7/2010

OTHER PUBLICATIONS

Chelly, Jacques E.; An intophoretic, fentanyl HCl patient-controlled transdermal system for acute postoperative pain management; Expert Opin. Pharmacother.; vol. 6; No. 7; pp. 1205-1214; Jun. 2005.

Grond et al.; Iontophoretic transdermal system using fentanyl compared with patient-controlled intravenous analgesia using morphine for postoperative pain management; British Journal of Anaesthesia; vol. 98; No. 6; pp. 806-815; Jun. 2007.

Minkovvitz et al.; Safety and tolerability of fentanyl iontophoretic transdermal system: Findings from a pooled data analysis of four clinical trials; Journal of Opioid Management; vol. 6; No. 3; pp. 203-210; May/Jun. 2010.

Sathyan et al.; Passive absorption of fentanyl from the fentanyl HCl iontophoretic transdermal system; Current Medical Research and Opinion; vol. 25; No. 2; pp. 363-366; Feb. 2009.

Viscusi, Eugene; Patient-controlled drug delivery for acute postoperative pain management: A review of current and emerging technologies; Regional Anesthesia and Paid Medicine; vol. 33; No. 2; pp. 146-158; Mar.-Apr. 2008.

\* cited by examiner

| Test name & ID | | Test sequencing | Test scheduling | | | | | | |
|---|---|---|---|---|---|---|---|---|---|
| | | | POST | Ready | Dosing | | | EOU | EOL |
| | | Predecessor tests | | Periodically w/ indicated period | Before enabling current | Periodically w/ indicated period | After disabling current | Periodically w/ indicated period | Periodically w/ indicated period |
| 1 | RAM Test | N/A | X | | | | | | |
| 2 | ROM Test | 1 | X | | | | | | |
| 3 | Calibration Data Integrity Test | 1,2 | X | 10 minutes | X | | | 10 minutes | |
| 4 | ADC and Reference Voltage Test | 1,2,3 | X | 1 minute | X | 1 minute | | 1 minute | |
| 5 | Oscillator Accuracy Test | 1,2,3,4 | X | 4 minutes | X | 20 seconds | | | |
| 6 | Anode/Cathode Voltage Difference Test | 1,2,3,4 | X | 1 minute | X | | X | 1 minute | |
| 7 | Rsense Accuracy Test | 1,2,3,4 | X | 1 minute | | | | 1 minute | |
| 8 | Output Current Off Test | 1,2,3,4,7 | X | 1 minute | | | X | 1 minute | |

FIG. 21

| Test name & ID | | Test sequencing | Test scheduling | | | | | | |
|---|---|---|---|---|---|---|---|---|---|
| | | Predecessor tests | POST | Ready | Dosing | | | EOU | EOL |
| | | | | | Before enabling current | Periodically w/ indicated period | After disabling current | | |
| 9 | Battery Voltage Test | 1,2,3,4 | X | Periodically w/ indicated period | | | | Periodically w/ indicated period | Periodically w/ indicated period |
| | | | | 10 minutes | | 1 minute | | 10 minutes | 10 minutes |
| 10 | Software Timer Integrity Test | 1,2,5 | | 10 minutes | | 1 minute | | | |
| 11 | Dose Count Integrity Test | 1,2,5 | | | | | Before counting dose | | |
| 12 | Analog Switch Validation Test | 1,2,3,4 | | On every detected button release | | | | | |
| 13 | Digital Switch Validation Test | 1,2 | | On second button release of double press | | | | | |
| 14 | Compromised Skin Barrier Test | 1,2,3,4,7 | | | | 1 second (after 1 min elapsed) | | | |
| 15 | Poor Skin Contact Test | 1,2,3,4,7 | | | | 1 second (after 4 min elapsed) | | | |
| 16 | High Output Current Test | 1,2,3,4,7 | | | | 1 second | | | |

FIG. 21 (CONT.)

SELF-TEST FOR ANALGESIC PRODUCT

CROSS REFERENCE TO RELATED APPLICATIONS

This application is a continuation of U.S. patent application Ser. No. 13/866,371, filed Apr. 19, 2013, titled "SELF-TEST FOR ANALGESIC PRODUCT," now U.S. Pat. No. 9,095,706, which is a divisional of U.S. patent application Ser. No. 13/476,960, filed May 21, 2012, titled "SELF-TEST FOR ANALGESIC PRODUCT," now U.S. Pat. No. 8,428,708, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to electrotransport drug delivery devices and methods of operation and use. These drug delivery devices may have improved safety. In particular, the invention is directed to drug delivery devices including automated self-testing.

BACKGROUND

A variety of drug delivery systems, including automatic drug delivery systems, are known. Because the consequences of delivering an inappropriate dosage (e.g., too much or too little) of a drug can be life threatening, it is of critical importance that drug delivery systems be extremely accurate. Drug delivery systems that are configured to deliver medication to patients must be configured to prevent even unlikely accidental delivery events. In particular, drug delivery systems that electrically deliver drug to a patient, including transdermal or other electroransport drug delivery devices, should ideally prevent accidentally providing drug to the patient.

The term "electrotransport" as used herein refers generally to the delivery of an agent (e.g., a drug) through a biological membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electro-osmosis, involves the flow of a liquid. The liquid contains the agent to be delivered, under the influence of an electric field. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent is transported.

In general, electrotransport devices use at least two electrodes that are in electrical contact with some portion of the skin, nails, mucous membrane, or other body surface. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, i.e., a cation, then the anode is the active or donor electrode, while the cathode serves to complete the circuit. Alternatively, if an agent is negatively charged, i.e., an anion, the cathode is the donor electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Passive flux control membranes, adhesives for maintaining device contact with a body surface, insulating members, and impermeable backing members are some other potential components of an electrotransport device that may be used.

Small, self-contained electrotransport drug delivery devices adapted to be worn on the skin for extended periods of time have been proposed. See, e.g., U.S. Pat. No. 6,171, 294, U.S. Pat. No. 6,881,208, U.S. Pat. No. 5,843,014, U.S. Pat. No. 6,181,963, U.S. Pat. No. 7,027,859, U.S. Pat. No. 6,975,902, and U.S. Pat. No. 6,216,033. These electrotransport agent delivery devices typically utilize an electrical circuit to electrically connect the power source (e.g., a battery) and the electrodes. The electrical components in such miniaturized iontophoretic drug delivery devices are also preferably miniaturized, and may be in the form of either integrated circuits (i.e., microchips) or small printed circuits. Electronic components, such as batteries, resistors, pulse generators, capacitors, etc., are electrically connected to form an electronic circuit that controls the amplitude, polarity, timing waveform shape, etc., of the electric current supplied by the power source. Other examples of small, self-contained electrotransport delivery devices are disclosed in U.S. Pat. No. 5,224,927; U.S. Pat. No. 5,203,768; U.S. Pat. No. 5,224,928; and U.S. Pat. No. 5,246,418.

One concern, particularly with small self-contained electrotransport delivery devices which are manufactured with the drug to be delivered already in them, is the potential for unintended delivery of drug because of electrical energy applied from an outside source, or because of an internal short. Any current or potential difference between the anode and cathode of the device may result in delivery of drug by a device contacting the skin, even if the device is not activated or in an off state. For example, drug may unintentionally be delivered if a current is applied through the devices or to a subject wearing a device, even if the device is in an off mode (even powered off). This risk, while hopefully unlikely, has not previously been addressed by electrotransport drug delivery devices.

Although an electrotransport device may include control circuitry and/or modules (e.g., software, firmware, hardware, etc.) configured specifically to regulate the current (and therefore the dosage of drug) applied when the device is "on," such devices do not typically monitor the devices when they are in an "off" state.

Described herein are methods, devices and systems for monitoring and controlling electrotransport drug delivery devices to detect and/or prevent delivery of drug by the device when it is in an off mode or state. In particular, described herein are devices, systems and methods that confirm that voltage or current is not applied between the electrodes (anode and cathode) of the device when it is in an "off" state or mode.

SUMMARY OF THE DISCLOSURE

In general, described herein are devices and methods including self-testing to prevent delivery of drug from an electrotransport drug delivery device when the device is not activated or in an off state.

For example, described herein are electrotransport drug delivery devices that prevent unwanted delivery of drug while in an off state. The device may include: an anode; a cathode; an activation circuit configured to apply current between the anode and cathode to deliver a drug by electrotransport when the device is in an on state and not in the off state; and an off-current module that is configured to automatically and periodically determine if there is a current flowing between the anode and cathode when the activation circuit is in the off state while powered on.

In general, the anode and/or cathode may connect to a source of the drug to be delivered, such as an analgesic like fentanyl and sufantanil within a gel matrix. The device may include a controller/processor or other electronic components (including software, hardware and/or firmware) forming the activation circuit and/or off-current module. In some variations the off-current module is integrated with other control systems (sub-systems) forming the device.

As used herein, a module, such as the off-current module, may include hardware, software, and/or firmware configured to perform the specified function (e.g., determine if a current is flowing between the anode and cathode). The module may include a combination of these, and may be a separate or separable region of the device or it may make use of shared components of the device (e.g., a microcontroller, resistive elements, etc.). For example, an off-current module comprises firmware, software and/or hardware configured to determine if there is a potential difference between the anode and the cathode when the activation circuit is in the off state while powered on. A module, such as the off-current module may include executable logic that operates on elements (e.g., a microcontroller) of the device. For example, the off-current module may include off-current monitoring logic controlling monitoring for the presence of a current (or indicator of current such as electrical potential, inductive or capacitive changes, etc.) between the anode and cathode when the device is otherwise in an off state.

In some variations of the device, systems and methods described herein the off-current module operates to monitor for and/or act upon identifying a current between the anode and cathode when the device is powered on but in an off state. Examples of off-states are provided below, but may include a ready state, a standby state, or the like, and may include any state during which the device is not in a dosing state and is not intended to deliver drug. The dosing state may be referred to as an on state and may indicate that the device is delivering drug. The off state described herein may occur when the device is otherwise powered on. In some variations, the off state includes the powered off state, while in some variations the off state does not include the powered off state, but only includes off states when the device is powered on.

In general, the off-current module may be configured to detect current flow between the anode and cathode in an off state either directly or indirectly. For example, in some variations the off-current module determines that current is flowing between the anode and cathode by monitoring for a voltage or a potential difference between the anode and cathode in the off state. For example, in some variations, the off-current module comprises software, firmware and/or hardware configured to determine if there is a change in capacitance between the anode and cathode when the activation circuit is in the off state while powered on. In one example an off-current module comprises software, firmware and/or hardware configured to determine if there is a change in inductance between the anode and cathode when the activation circuit is in the off state while powered on. Thus, current may be inferred to be flowing between the anode and cathode by monitoring indirectly for presence of or changes in potential difference (e.g., voltage), capacitance, inductance, or the like, between the anode and cathode of the device.

In general, the off-current module may indicate that current is flowing between the anode and cathode only when the detected current (or an indicator of current such as potential difference, inductance, capacitance, etc.) is above a threshold value. The threshold value is typically above the noise threshold for the device/system. This threshold may be predetermined. For example, in some variations the off-current module may comprise a sensing circuit that independently determines an anode voltage and a cathode voltage and compares the potential difference between the anode voltage and cathode voltage to a threshold value. For example, an off-current module may be configured to indicate that there is a current flowing between the anode and cathode when the activation circuit is in the off state while powered on where the current flowing is above an Output Current Off Threshold. Any appropriate Output Current Off Threshold may be used, e.g., about 1 $\mu$A, 3 $\mu$A, 5 $\mu$A, 9 $\mu$A, 10 $\mu$A, 15 $\mu$A, 25 $\mu$A, 30 $\mu$A, 50 $\mu$A, 100 $\mu$A, etc. In some variations the Output Current Off Threshold is about 9 $\mu$A.

An electrotransport device may include a switch connected between a reference voltage source and a sense resistor, so that the off-current module is configured to close the switch periodically to determine the potential difference between the anode voltage and cathode voltage.

Thus, in some variations the off-current module may be configured to determine if there is a potential difference between the anode and the cathode before the device allows current to travel through the anode and cathode. For example, the off-current module, be detecting if there is a current flowing between the anode and cathode even when the device is otherwise "off", may trigger an alert that there is a leak current. In some variations the alert may include a shutdown of the device, and/or a visible (e.g., indicator light) or audible (e.g., beeping, buzzing, etc.) notification.

The off-current module may be configured to monitor at any periodic and/or automatic interval. For example, the off-current module may be configured to determine if there is a current flowing between the anode and cathode when the activation circuit is in the off state at least once per minute, once per 10 ms, once per 100 ms, once per 500 ms, once per 1 min, once per 2 min, once per 3 min, once per 4 min, once per 5 min, once per 10 min, once per 15 min, etc. For example, the off-current module may be configured to determine if there is a current flowing between the anode and cathode when the activation circuit is in the off state between at least once every 10 ms and once every 10 minutes.

In some variations an off-current module may be configured to wait some length of time (e.g., at least 10 ms) before determining if there is a current flowing between the anode and cathode when the activation circuit is in the off state. This length of time may be at least 4 ms, at least 10 ms, at least 15 ms, at least 30 ms, etc.

In some variations the electrotransport devices described herein have a two-part structure. The two-part structure may include: an electrical module including the activation circuit and the off-current module; and a reservoir module including the anode and the cathode and a source of drug to be delivered; wherein the electrical module and reservoir module are configured to be combined prior to application to a patient. In some variations, the off-current module may not be enabled until the electrical module and reservoir module are combined.

As mentioned above, in some variations, the off-current module may be configured to indicate that there is a current flowing between the anode and cathode when the activation circuit is in the off state while powered on, where the current flowing is above an Output Current Off Threshold. For example, the Output Current Off Threshold may be about 9 µA.

Also described herein are electrotransport drug delivery devices that prevent unwanted delivery of drug while in an off state. The device may include: a reservoir module including: an anode, a cathode and a source of drug; an electrical module including: an activation circuit configured to apply current between the anode and cathode to deliver a drug by electrotransport when the device is in an on state and not in the off state; and an off-current module, the module configured to automatically and periodically determine if there is a current flowing between the anode and the cathode greater than an Output Current Off Threshold of 9 µA when the activation circuit is in the off state while powered on; wherein the reservoir module and the electrical module are configured to be combined before being applied to a patient.

Methods of automatically and periodically confirming that drug will not be delivered by an electrotransport drug delivery device when the device is in an off state are also described herein. For example, a method of automatically and periodically confirming that drug will not be delivered by an electrotransport drug delivery device when the device is in an off state while powered on may include the steps of: determining if there is a current flowing between an anode and a cathode of the electrotransport drug delivery device when the electrotransport drug delivery device is in an off state while powered on, wherein the electrotransport drug delivery device includes an activation circuit that is configured to apply current between the anode and the cathode to deliver a drug when the device is in an on state and not in the off state; and triggering an indicator if there is a current flowing between the anode and cathode that is greater than an Output Current Off Threshold when the electrotransport drug delivery device is in an off state while powered on. The method may also include repeating the determining step periodically while the activation circuit is in an off state. In some variations the method also includes repeating the determining step at least once every 10 minutes while the activation circuit is in an off state and the device is powered on.

As mentioned above, any appropriate Output Current Off Threshold may be used. For example, an Output Current Off Threshold may be about 9 µA. The step of determining if there is a current flowing between the anode and cathode of the electrotransport drug delivery device may include independently determining an anode voltage and a cathode voltage and comparing the potential difference between the anode voltage and cathode voltage to the threshold value. Any appropriate threshold (e.g., above noise) value may be used. For example, a threshold value may be about 2.5 V. In some variations the threshold value is about 0.85 V.

In some variations, the step of determining if there is a current flowing between the anode and cathode of the electrotransport drug delivery device may include independently connecting a reference voltage source and a sense resistor with each of the anode and cathode to determine the potential difference between the anode voltage and cathode voltage.

Any of the methods described herein may also include activating the activation circuit to enter the on state and applying current between the anode and the cathode after determining that no current above the Output Current Off Threshold is flowing between the anode and cathode while the electrotransport drug delivery device is in the off state.

In any of the devices, systems and methods described herein, the electrotransport device may trigger an indicator and/or modify the state of the device when a current is detected or inferred, between the anode and cathode while the device is in the off state. For example, in some variations, the device may trigger an indicator comprising a visible, audible and/or tactile alert or alarm. For example, an indicator may include illuminating a light and/or sounding an alarm on the device. In some variations, the system may transmit (e.g., electronically, wirelessly, etc.) a signal to another device such as a computer, handheld device, server, and/or monitoring station indicating the alarm status of the device.

In any of the variations described herein, the device, system or method may be configured so that when the off-current module senses or infers a current is flowing between the anode and cathode while the device is in the off state (e.g., while the device is otherwise powered on), the triggering of an indicator may include switching the device to an end of life state, e.g., such as performing a device shutdown. Thus, when the off-current module determines or infers that current is flowing between the anode and cathode when the device is not supposed to be delivering drug, the device (e.g., the off-current module) may prevent further unwanted drug delivery.

In general, when the device or system (or methods of operating them) is described as detecting current flowing between the anode and cathode of the device when the device is not supposed to be delivering drug (e.g., when an off-current module detects current flow between the anode and cathode in an off state) this may be interpreted in some variations as determining if there is a current above some threshold flowing between the anode and cathode. As described above, depending on the way in which the off-current module detects or infers current flow between the anode and cathode, this threshold may be a current threshold, a potential difference (i.e., voltage) threshold, an inductive threshold, a capacitive threshold, or the like. The threshold may be predetermined (preset) in the device.

BRIEF DESCRIPTION OF THE DRAWINGS

FIG. 21 shows Table 1, indicating one variation of the sequencing of self-testing (the mode diagram of FIG. 12 may correspond with this table).

DETAILED DESCRIPTION

Figure 1A:
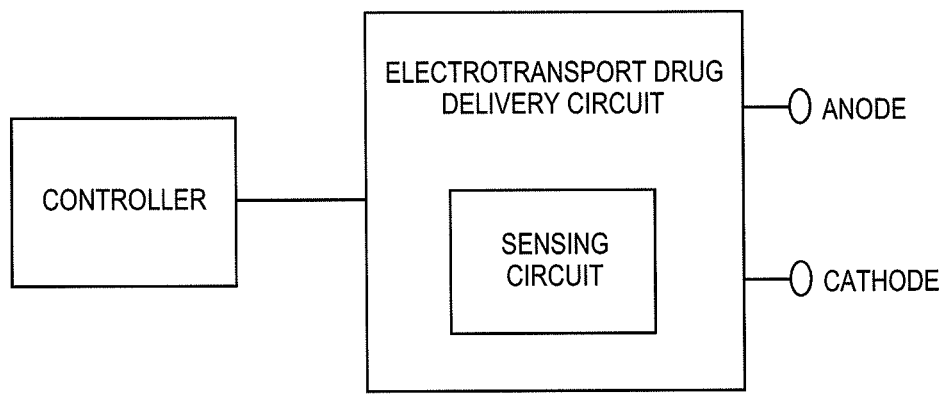
FIG. 1A is a block diagram of an exemplary potential difference detection system including a controller, an electrotransport drug delivery circuit, a sensing circuit, an anode and a cathode.

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as defined by the appended claims.

One method for transdermal delivery of active agents involves the use of electrical current to actively transport the active agent into the body through intact skin by electrotransport. Electrotransport techniques may include iontophoresis, electroosmosis, and electroporation. Electrotransport devices, such as iontophoretic devices are known in the art. One electrode, which may be referred to as the active or donor electrode, is the electrode from which the active agent is delivered into the body. The other electrode, which may be referred to as the counter or return electrode, serves to close the electrical circuit through the body. In conjunction with the patient's body tissue, e.g., skin, the circuit is completed by connection of the electrodes to a source of electrical energy, and usually to circuitry capable of controlling the current passing through the device when the device is "on" and delivering current. If the substance to be driven into the body is ionic and is positively charged, then the positive electrode (the anode) will be the active electrode and the negative electrode (the cathode) will serve as the counter electrode. If the ionic substance to be delivered is negatively charged, then the cathodic electrode will be the active electrode and the anodic electrode will be the counter electrode.

A switch-operated therapeutic agent delivery device can provide single or multiple doses of a therapeutic agent to a patient by activating a switch. Upon activation, such a device delivers a therapeutic agent to a patient. A patient-controlled device offers the patient the ability to self-administer a therapeutic agent as the need arises. For example, the therapeutic agent can be an analgesic agent that a patient can administer whenever sufficient pain is felt.

As described in greater detail below, any appropriate drug (or drugs) may be delivered by the devices described herein. For example, the drug may be an analgesic such as fentanyl (e.g., fentanyl HCL) or sufantanil.

In some variations, the different parts of the electrotransport system are stored separately and connected together for use. For example, examples of electrotransport devices having parts being connected together before use include those described in U.S. Pat. No. 5,320,597 (Sage, Jr. et al); U.S. Pat. No. 4,731,926 (Sibalis), U.S. Pat. No. 5,358,483 (Sibalis), U.S. Pat. No. 5,135,479 (Sibalis et al.), UK Patent Publication GB2239803 (Devane et al), U.S. Pat. No. 5,919, 155 (Lattin et al.), U.S. Pat. No. 5,445,609 (Lattin et al.), U.S. Pat. No. 5,603,693 (Frenkel et al.), WO 1996036394 (Lattin et al.), and US 2008/0234628 A1 (Dent et al.).

In general, the systems and devices described herein include an anode and cathode for the electrotransport of a drug or drugs into the patient (e.g., through the skin or other membrane) and a controller for controlling the delivery (e.g., turning the delivery on or off); all of the variations described herein may also include an off-current module for monitoring the anode and cathode when the activation circuit is in the off state while still powered on to determine if there is a potential and/or current (above a threshold value) between the anode and cathode when the controller for device has otherwise turned the device "off" so that it should not be delivering drug to the patient. The controller may include an activation controller (e.g., an activation module or activation circuitry) for regulating the when the device is on, applying current/voltage between the anode and cathode and thereby delivering drug.

Throughout this specification, unless otherwise indicated, singular forms "a", "an" and "the" are intended to include plural referents. Thus, for example, reference to "a polymer" includes a single polymer as well as a mixture of two or more different polymers, "a contact" may refer to plural contacts, "a post" may indicate plural posts, etc.

As used herein, the term "user" indicates anyone who uses the device, whether a healthcare professional, a patient, or other individual, with the aim of delivering a therapeutic agent to a patient.

In general, the off-current module may include hardware, software, firmware, or some combination thereof (including control logic). For example, as illustrated in FIG. 1A, a system may include an anode, cathode and sensing circuit. The sensing circuit may form part (or be used by) the off-current module to sense any current between the anode and cathode when the device is otherwise off. The device may also include a controller controlling operation of the device. The controller may include a processor or ASIC that includes the off-current module.

In general, and off-current module may also be referred to as a type of self-test that is performed by the device. In some variations, the off-current module includes or is referred to as an anode/cathode voltage difference test or off-current test, because in some variations it may determine if there is a voltage difference between the anode and cathode when the device should be off.

Figure 1B:
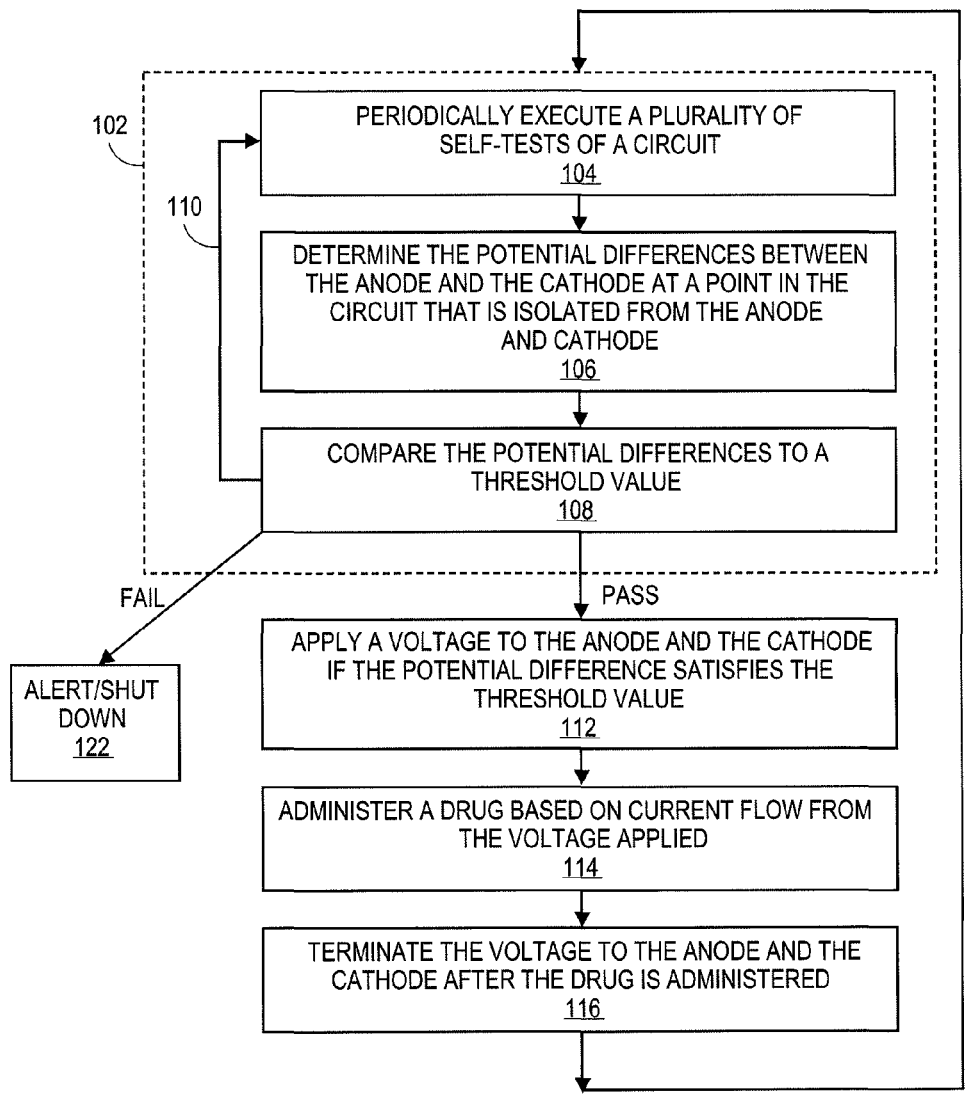
FIG. 1B is a flow diagram of a method of an exemplary automated self-test of an electrotransport drug delivery system configured as an off-current (or anode/cathode voltage difference) test.

FIG. 1B illustrates a simplified version of one method of performing an anode/cathode voltage difference test (also referred to as an off-current test). Initially, when the device is powered on but it is not activated to deliver drug (e.g., is in powered on but in an off state), the device may periodically perform any number of self-tests while in this "ready" mode. In particular, the device may perform the off-current test to confirm that while the device is otherwise off, there is not a significant current flowing (which may be inferred, e.g., by determining that there isn't a potential difference above a threshold level sufficient to deliver drug to the patient) between the anode and cathode. In embodiments in which the current is determined by monitoring potential difference, this potential difference may readily be determined by examining the difference between the voltage at the anode and the voltage at the cathode. Any other subsystem or method of measuring and/or inferring current flow between the anode and cathode may also be used as long as the testing method itself does not result in undesirable drug delivery.

Returning to FIG. 1B, in the initial step 102 the self-test(s) such as the off-current self-test may be periodically and automatically performed while the device is in the ready mode. The off-current self-test may be timed and executed by control logic (e.g., executing on a controller) which may be part of another controller or may be a controller. In general the controller (or portion of a controller) performing the off-current test may be referred to as an off-current module. The self-test may be triggered at regular intervals, such as every 30 seconds, every minute, every two minutes, etc. Once the self-test is triggered, in some variations it may be performed by determining the difference between the voltage at the anode and the voltage at the cathode in a manner that does not trigger release of drug. For example, the determination of the voltage of the anode may be isolated from the determination of the voltage of the cathode 104. The difference in the voltages may next be compared to a threshold value 106, which may be referred to as the off-current threshold. Examples of this threshold value include 0.5V, 0.75V, 0.85V, 2.5V, etc. If the difference is less than the threshold value than the device "passes" the self-test, and may continue in "ready" mode 110, or, if the activation of the device has been triggered (e.g., by pressing button), the device my begin delivering drug 112-116.

Alternatively, if a leak current is detected, e.g., when the voltage difference is greater than (or equal to) the threshold voltage (fail 122), the device may trigger an alert and/or may shut down to prevent unwanted delivery of drug.

Example 1

Two-Part System

Described below is one example of a two part system that may include self-tests including in particular an anode/cathode voltage difference test. For example, in some variations the devices including the off-current self-test are configured as two-part electrotransport therapeutic agent delivery devices, such as iontophoresis devices, in which the two parts of the device are provided separately and assembled to form a unitary, powered-on device at the point of use—that is to say just prior to use. In this example, one part of the device, which may be referred to herein as the electrical module, holds essentially all of the circuitry, as well as the power source (e.g. battery), for the device; and the other part, which may be referred to herein as the reservoir module, contains the therapeutic agent to be delivered along with electrodes and hydrogels necessary to deliver the therapeutic agent to a patient. The device is configured such that the power source is kept electrically isolated from the rest of the circuitry in the electrical module until the electrical module is combined with the reservoir module. Thus, embodiments provided herein permit the combination of the electrical module and the reservoir module, whereby in a single action the two modules form a single unit and the battery is introduced into the circuitry, thereby powering on the device, in a single action by the user.

As used herein, the term simultaneous, and grammatical variants thereof, indicates that two or more events occur at about the same time and/or that they occur without any intervening step. For example, when connection of the modules occurs simultaneously with connection of the battery into the circuit, the term "simultaneously" indicates that when the modules are connected, the battery is connected into the circuit at about the same time, in a single action by the user, and that there is no additional step necessary on the part of the user to connect the battery to the circuit. The term "substantially simultaneous" and grammatical variants indicates that two events occur at about the same time and no significant action is required by the user between the two events. For the sake of illustration only, such a significant action could be the activation of a separate switch (other than the herein-described power-on switches), removal of a tab, or other action to connect the battery in the electrical module to the circuitry therein upon connection of the two modules to one another.

Unless otherwise modified herein, the term "to break" and grammatical variants thereof refers to destroying or deforming something to the point that it is no longer operable for its intended purpose.

An electrotransport device may be assembled before use for electrotransport delivery of ionic compounds (e.g., ionic drugs such as fentanyl and analogs, polypeptides, and the like) through a surface, such as skin. An electrotransport device may comprise a top or upper portion, herein referred to as an electrical module, and a bottom or lower portion, herein referred to as a reservoir module. The electrical module may contain circuitry (e.g. a printed circuit board), a power source (e.g. a battery), one or more power-on switches and such other circuitry as may be deemed desirable for operation of the device (such as an activation switch, a controller, a liquid crystal diode (LCD) display, a connector, a light emitting diode (LED), an audible indicator (e.g. a sound transducer), or combinations thereof), as well as electrical output contacts for electrically connecting the electrical module to a reservoir module. When obtained by the user, the electrical module is separated from the reservoir module. In this state, the battery is maintained outside of the electrical circuit (though within the electrical module), thereby preventing the battery from discharging through the circuit prior to use. Because the battery is electrically isolated from the circuit prior to combining the electrical and reservoir modules, the circuitry has essentially no electrical charge applied to it prior to combination of the two modules, rendering the circuitry far less susceptible to corrosion than if the battery were in the circuit. In some variations the off-current module may be configured to operate even when the two parts of the device/system are not connected (e.g., even with the device powered off, and/or with the battery driving drug delivery disconnected). Thus, a separate power source/batter may power the off-current module in some variations. In other variations the off-current module may be configured to operate when the device is in an off state, but otherwise powered on (e.g., when the two halves of the system/device are connected). In any of the variations described herein the off-current module may be electrically isolated from the drug delivery sub-components of the device/system. Thus, even if a short occurs in the drug delivery component of the device, the off-current module may operate.

The reservoir module may contain electrodes and reservoirs for delivery of therapeutic agent to a patient. At least one reservoir may contain the therapeutic agent to be delivered. At least one counter reservoir is provided, which generally contains no therapeutic agent, though in some embodiments it is possible for the counter reservoir to contain therapeutic agent. Prior to being connected to the electrical module, the reservoir module is maintained both physically and electrically isolated from the electrical module. For example, one or both of the modules may be sealed in a pouch, such as a plastic or foil pouch, in order to prevent contamination with water, particulates, vapors, etc. As a non-limiting example, both the electrical and the reservoir modules may be sealed in the same pouch. As a further non-limiting example, the reservoir module may be sealed in a pouch and the electrical module left outside the sealed pouch. In other non-limiting examples, the two modules may be sealed in separate pouches.

Prior to use (e.g. just prior to use) the electrical module is combined with the reservoir module to form a single unit, which in a single action, connects the battery into the circuit and powers the device on. The terms "prior to use" and "just prior to use" are described in more detail hereinafter. In general, these terms are intended to indicate that the two parts of the device are combined by a user, and that the device is then used to deliver therapeutic agent to a patient within a predetermined window of time—e.g. from 0 to 8 hrs. or from 0 to 72 hours—after the two parts of the device are combined. This predetermined window of time may vary, depending upon the therapeutic agent, the amount of agent to be delivered, requirements of various regulatory agencies, etc. For the sake of clarity, it is to be understood that combination of the electrical and reservoir modules is postponed after manufacture and is carried out at the point of use so that during shipping and storage the power source enclosed within the electrical module is electrically isolated from the circuitry until the two modules are combined by the user.

As stated before, combination of the electrical and reservoir modules connects the battery into the circuit to achieve a powered on state, without any additional action required on the part of the user. For example, there is no need for the user to activate a power switch or remove a tab in order to connect the battery into the circuit. Once the two modules have been properly combined, power is supplied to the circuitry. The circuitry can then operate normally. Normal operation may include various circuitry tests, operation of various indicators (such as the aforementioned LCD, LED and sound transducers), setting of various logic flags, detection of error states and/or logic flags, etc. Normal operation also includes reception of an activation signal, e.g. through an activation button or switch, and providing power to the electrodes through electrical outputs connected to electrical inputs on the reservoir module.

In addition to reducing corrosion and battery discharge prior to use, another advantage of the device is that the electrical outputs from the electrical module and inputs to the reservoir module (i.e. the contacts between the two modules) are electrically and physically separated from the power-on switches that connect the battery into the circuit. This is advantageous, at least because it allows the power-on switches, which connect the battery into the circuit, to be kept entirely internal to the electrical module. This in turn allows the contacts that comprise the power-on switches to be kept contaminant-free, as the electrical module is at least in some embodiments sealed against contaminants, such as water (including water vapor) and/or particulates. As described herein, a power-on switch is closed by an actuator through an elastomeric seal, which permits the battery to be connected into the circuit without the contacts that comprise the switch being exposed to the environment external to the electrical module.

In some embodiments, two or more power-on switches are employed. In some particular embodiments, the power-on switches are physically remote from one another—e.g. on the order of from 0.1 cm to several cm. In some embodiments, the switches are at least 0.5 cm from one another.

As the two modules form a unitary device, they advantageously include one or more mechanical coupler pairs to hold the two modules together. Such coupler pairs can include snap-snap receptacle pairs, which are in some embodiments designed to become inoperative (deform and/or break) if the two modules are forced apart after they are combined. Thus, devices described herein are well-suited for one time use, as they can be adapted to embody mechanical means for ensuring that the device is used only once.

In some embodiments, the device may alternatively, or additionally, employ electrical means for ensuring that the device is used only once. For example, an electrical means may employ a controller in the electrical module which increments a power-on counter when the device is powered on. In such embodiments, before or after the controller increments the counter, it detects the number of counts on the counter, and if it finds that the power-on counts exceed some predetermined value, it executes a routine to power the device off. As a non-limiting example the counter may initially be set to zero upon manufacturing. The device may then be briefly powered on by an external power supply during post-manufacturing testing, which the controller interprets as one power-on event, and thus increments the power-on counter by 1 count. Then when the device is assembled by the user prior to use, the controller interprets the connection of the battery into the circuit as a power-on event, and increments the power-on counter by 1. The controller then detects the count on the counter. If the count is 2 or less, the controller permits the device to operate normally. If however, the count is 3 or more, the controller initiates a power-off sequence.

As a second, non-limiting example, the counter may initially be set to zero upon manufacturing. The device may then be briefly powered on by an external power supply during post-manufacturing testing, which the controller interprets as one power-on event, and thus increments the power-on counter by 1 count. Then when the device is assembled by the user prior to use, the controller detects the count on the counter. If the count is 1 or less, the controller increments the power-on counter and permits the device to operate normally. If however, the count is 2 or more, the controller initiates a power-off sequence.

Although reference is made here to counting power-on sequences, other events may be counted, either in place of power-on events, in addition to power-on events, or as a proxy for power-on events.

The power off sequence can be a sequence such as described in U.S. Pat. No. 6,216,003 B1, which is incorporated herein in its entirety.

In some embodiments, the device combines both mechanical (e.g. one-way snaps) and electrical (e.g. power-on counter) means to ensure that the device cannot be used more than once.

A single use device/system may include multiple administrations of a therapeutic agent, e.g. within a particular window of time after the device has been powered on. The duration of time during which therapeutic agent may be administered and/or the number of total doses permitted to be administered by the device may be predetermined and programmed into a controller. Means for controlling the number of doses that may be administered and/or the period during which therapeutic may be administered are described e.g. in U.S. Pat. No. 6,216,003 B1, which is incorporated herein in its entirety. For the sake of clarity, the term "single use" is not intended to limit the device to a single administration of drug. Rather, the term "single use" is intended to exclude use of the device on more than one patient or on more than one occasion; it is also intended to exclude the use of an electrical module with more than one reservoir module and/or the reservoir module with more than one electrical module and/or detachment of the reservoir module from the electrical module and reattachment. Thus, single use feature is in some embodiments employed to prevent the patient or another from saving drug and using it at a later time. In some embodiments, such a feature may be employed to prevent abuse of the therapeutic agent.

In at least some embodiments of the device described herein, the device is configured to prevent contamination of the circuitry before and during use in order to reduce the likelihood of device malfunction. For example, the use environment may include emergency room, operative, post-operative or other medical treatment environments, in which potential particulate and liquid are prevalent. Accordingly, at least some embodiments of the device are configured so that one or more seals are formed in order to exclude ambient contaminants from ingress into the working parts of the device, such as in particular the circuitry. In some embodiments, one or more seals are formed around electrical contacts between the electrical outputs on the electrical module and the electrical inputs on the reservoir module.

In some embodiments, the power-on contacts are sealed from ingress of contaminants, such as particulates and fluids.

In particular embodiments, the power-on contacts are sealed before the modules are combined, during the act of combination, and after the two modules are combined. In at least some such cases, the power-on contacts may be actuated (switched to a closed position) by an actuator that acts through an interposed elastomer, which maintains an impermeable seal while at the same time being deformed by an actuator (such as a post or other elongate member) to press the power-on contact into a closed position.

Other seals are possible and may be desirable. For example, a seal may be formed between the two parts (modules) when they are combined.

The device described herein may be appreciated by the person skilled in the art upon consideration of the non-limiting examples, which are depicted in the accompanying figures. Starting with FIG. 2A, an exemplary electrotransport device 10 is depicted. The device comprises two parts—an upper part, referred to herein as the electrical module 20—and a lower part, referred to herein as the reservoir module 30. The electrical module 20 includes an electrical module body 200, which has a top (proximal) surface 220 and a bottom (distal) surface (not depicted in this view). The module body 200 has a rounded end 234 and a squared off end 254. The top surface 220 includes a window or aperture 204 for viewing an LCD display 208, an activation button 202 and an LED window or aperture 232. An alignment feature 206 is also visible in this view.

The reservoir module 30 includes a reservoir module body 300, which supports electrodes, reservoirs (see description herein) and input contacts 316. In this view, there can be seen upper surface 320, on which input contact seals 322, circumscribe the input contacts 316. The seals 322 form contaminant-impervious seals with corresponding members on the electrical module 20 (see description herein). The upper surface 320 of the reservoir module body 300 has a rounded end 352 and a squared off end 356. Also visible are snap receptors 310 and 312, which are configured to cooperate with corresponding snaps on the lower surface of the electrical module 20. In some embodiments, the snaps 310 and 312 are of different dimensions so that each can receive a snap of the correct dimension only, with the result that the device 10 cannot be assembled in the wrong orientation. As a visual aid to proper alignment of the two modules 20, 30, the reservoir module 30 also has an alignment feature 306, which a user can align with the alignment feature 206 on the electrical module 20 to ensure that the two modules 20, 30 are properly aligned.

Also visible in this view is a recess 314, which in some embodiments is of such a shape as to accept a complementary protruding member on the lower surface of the electrical module 20 in one orientation only. The recess 314 and the protuberance on the electrical module 20 thereby perform a keying function, further ensuring that the two modules can be assembled in one orientation only and/or guiding the user to assemble the two modules in the correct orientation. Another illustrative and non-limiting keying (alignment) feature is the asymmetry of the electrical module 20 with respect to the reservoir module 30. As depicted e.g. in FIG. 2A, the rounded end 234 of the electrical module 20 corresponds to the rounded end 352 of the reservoir module; and the squared off end 254 of the electrical module 20 corresponds to the squared off end 356 of the reservoir module. The resulting asymmetry helps the user align the electrical module 20 with the reservoir module 30 and ensures that user can assemble the two modules in only one orientation. While the rounded end is depicted in this illustration as being distal to the viewer, one of skill in the art will recognize that this is but one possible orientation. As a non-limiting example, the rounded portion may be on the other end or one of the sides of the device. Additional keying features are discussed in more detail herein.

Also depicted in this view is one power-on post 318, which protrudes from the upper surface 320 of the reservoir module 30. The power-on post 318 is configured to contact a corresponding feature on the electrical module to actuate power-on switches, thereby electrically connecting the battery within the electrical module 20 into the circuitry contained therein. These features will be described in greater detail below. However, it should be noted that, while there is only one power-on post 318 depicted in this view, one of the intended power-on posts is obstructed by the perspective of the device. In some embodiments at least two posts and at least two power-on switches are considered advantageous, in that this is considered the minimum number of switches necessary to electrically isolate the battery from the rest of the circuit prior to use. However, this number is merely illustrative and any number of posts and power-on switches may be employed in the devices described herein.

Similarly, while there are two input contacts 322 depicted, and it is considered necessary that there be at least two such contacts—one positive and one negative—this number is also illustrative only; and any number of contacts—e.g. two positive and one negative, one positive and two negative, two positive and two negative—equal to or greater than two may be employed in devices according to this invention.

Figure 2A:
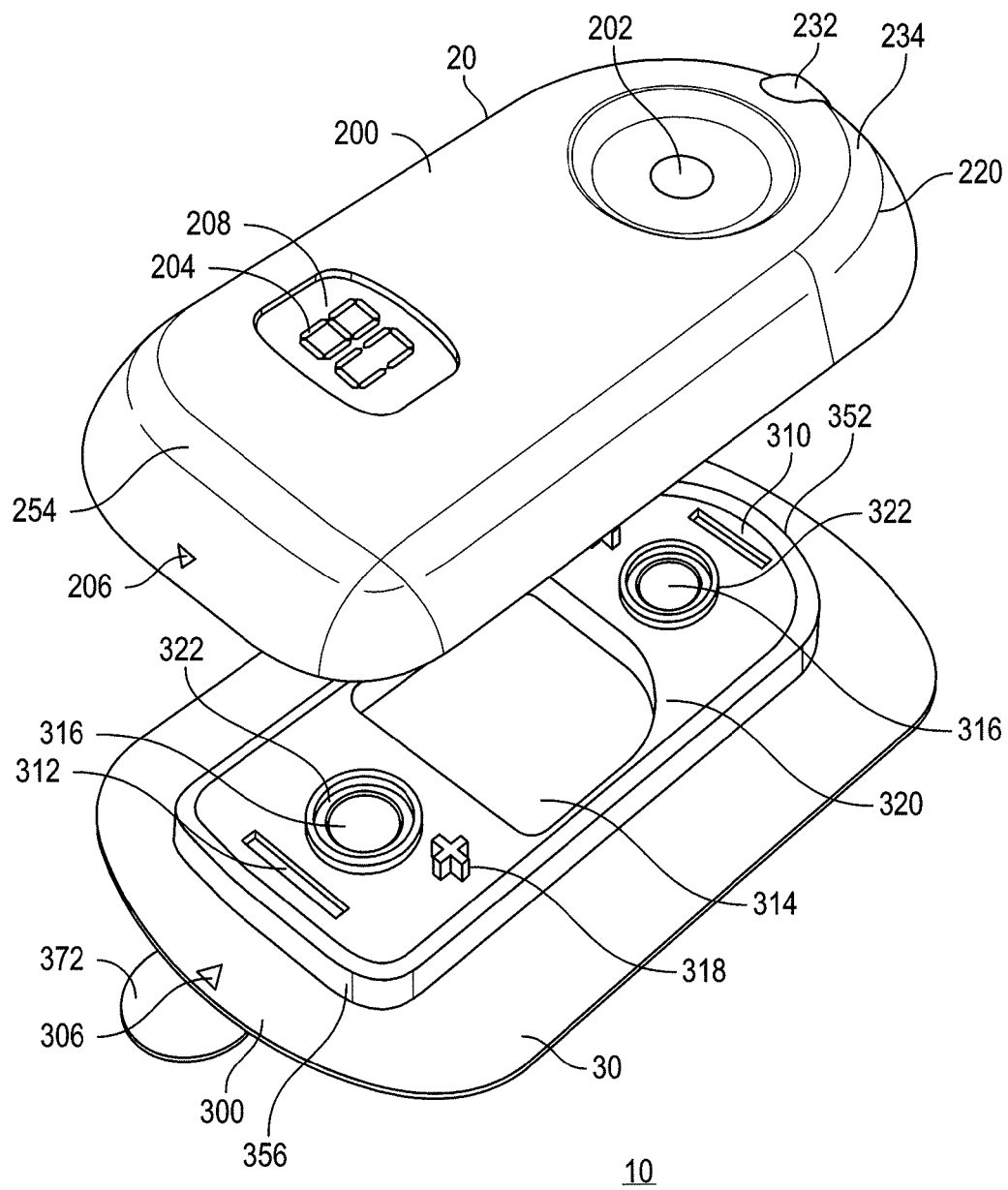
FIG. 2A illustrates an exemplary therapeutic agent delivery system in two parts.
Figure 2B:
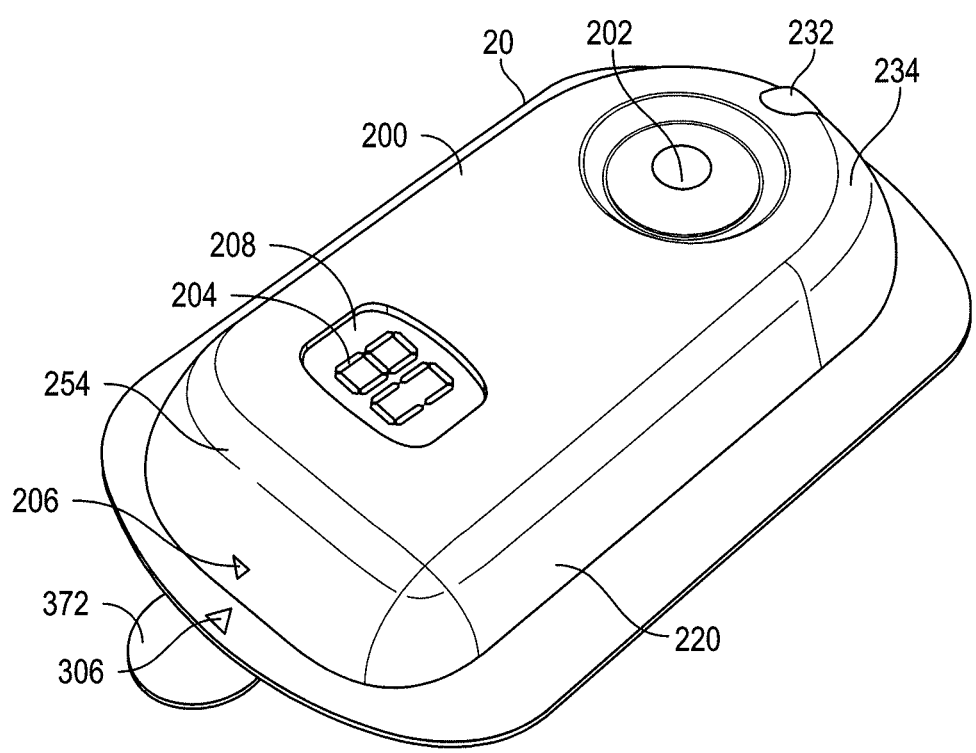
FIG. 2B shows the exemplary system of FIG. 1 combined to form a single, unitary device.

The two modules 20, 30 are combined (assembled) prior to use to form the unitary device 10 depicted in FIG. 2B, in which those parts that are visible in FIG. 2B have the same numbers as used in FIG. 2A.

Figure 3:
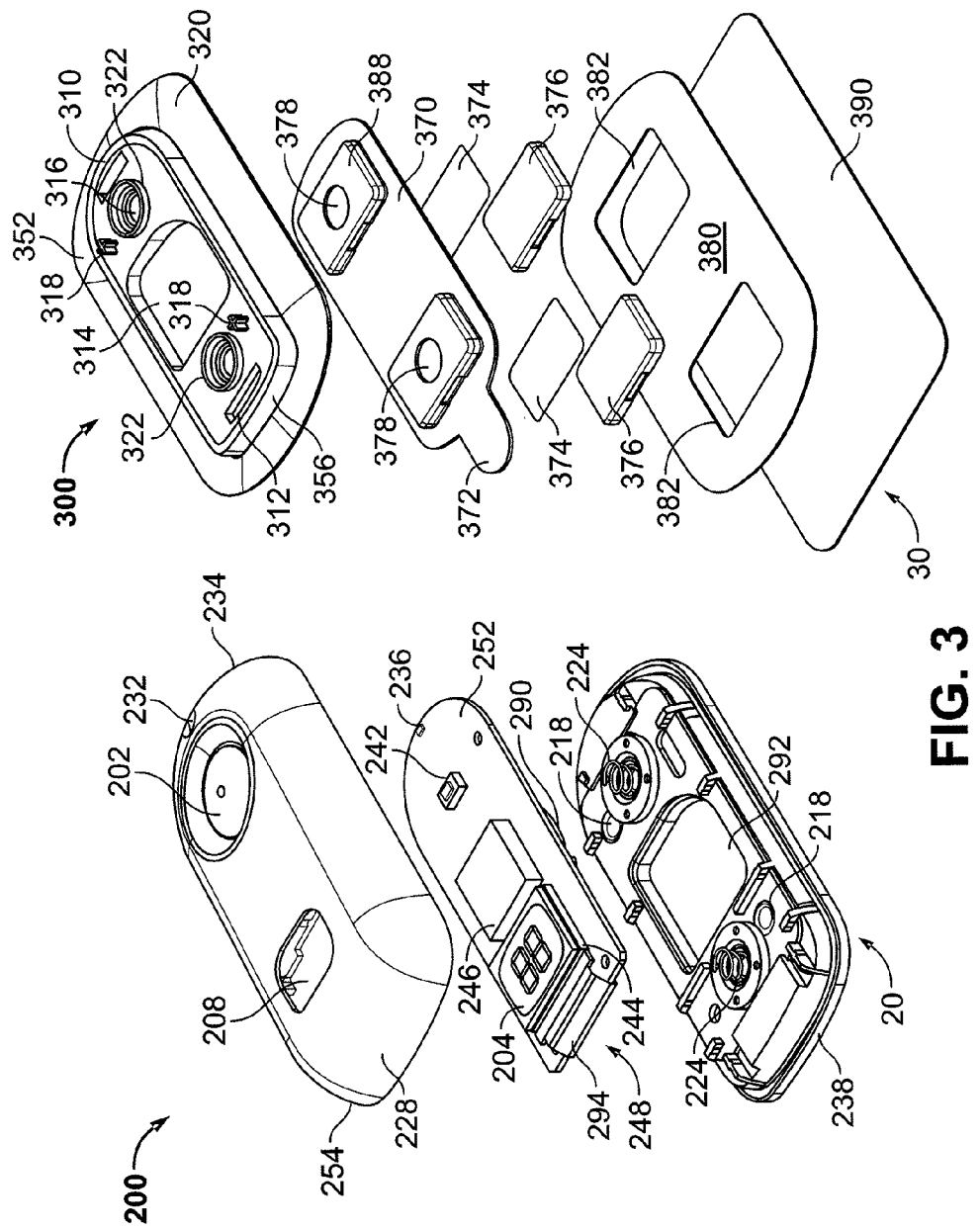
FIG. 3 shows an exploded perspective view of a two-part device.

The device 10 may be further understood by considering FIG. 3, in which the electrical module 20 and the reservoir module 30 are depicted in exploded perspective views. In the left side of FIG. 3, electrical module 20 is visible with upper electrical module body 228, lower electrical module body 238 and inner electrical module assembly 248. Visible on the upper electrical module body 228 are the activation button 202, the LED aperture or window 232, the LCD aperture or window 208. While it is also desirable in some embodiments to have an alignment feature on the upper electrical module body 228, this view does not include such an alignment feature.

Visible on the lower electrical module body 238 are the upper (proximal) surface of the elastomeric power-on receptacles 218 as well as springs 224. The function of the springs 224 will be described in more detail below. At this point it is noted that the springs 224 provide bias for connectors on the opposite side of the lower electrical module body 238.

The electrical circuit assembly 248 comprises a controller 244 beneath an LCD display 204 an LED 236 and an activation switch 242, all of which are arranged on a printed circuit board (PCB) 252. Also barely visible in this exploded view is the battery 290 on the lower side of PCB 252. The battery 290 fits within battery compartment 292 on the lower electrical module body 238. A flex circuit 294, which provides an electrical connection from the PCB 252 to the LCD display 204, is also depicted in this view. The LCD display 204 may be configured to communicate various data to a user, such as a ready indicator, a number of doses administered, a number of doses remaining, time elapsed since initiation of treatment, time remaining in the device's use cycle, battery level, error codes, etc. Likewise the LED 236 may be used to provide various data to a user, such as indicating that the power is on, the number of doses delivered, etc. The electrical circuit assembly 248 may also include a sound transducer 246 which can be configured to provide an audible "power on" signal, an audible "begin dose administration" signal, an audible error alarm, etc.

The reservoir module 30 appears in exploded perspective view in the right hand side of FIG. 3. The reservoir module 30 comprises a reservoir body 300, an electrode housing 370, an adhesive 380 and a release liner 390. The upper surface 320 of reservoir body 300 includes the recess 314, power-on posts 318, input connectors 316, seals 322 and coupler receptacles 310 and 312. The electrode housing 370 includes reservoir compartments 388. Electrode pads 374 and reservoirs 376 are inserted within the reservoir compartments 388. The electrodes 374 make contact with the input contacts 316 through the apertures 378. The adhesive 380, which provides means for attaching the device 10 to a patient, has apertures 382, through which reservoirs 376 contact the skin of a patient when the adhesive 380 is attached to a patient. The removable release liner 390 covers the reservoirs 376 and the reservoirs 376 prior to use, and is removed in order to allow the device 10 to be attached to a patient. Assembled, the electrode pads 374 contact the underside of the input connectors 316 through apertures 378, providing an electrical connection between the input connectors 316 and the reservoirs 376. Connection between the reservoirs 376 and the patient's skin is made through the apertures 382 after the release liner 390 is removed. Also visible in this view is a tab 372, which can be used to remove the electrode housing 370 from the reservoir body 300 for disposal of the reservoirs 374, which in some embodiments contain residual therapeutic agent, after the device 10 has been used.

Figure 4:
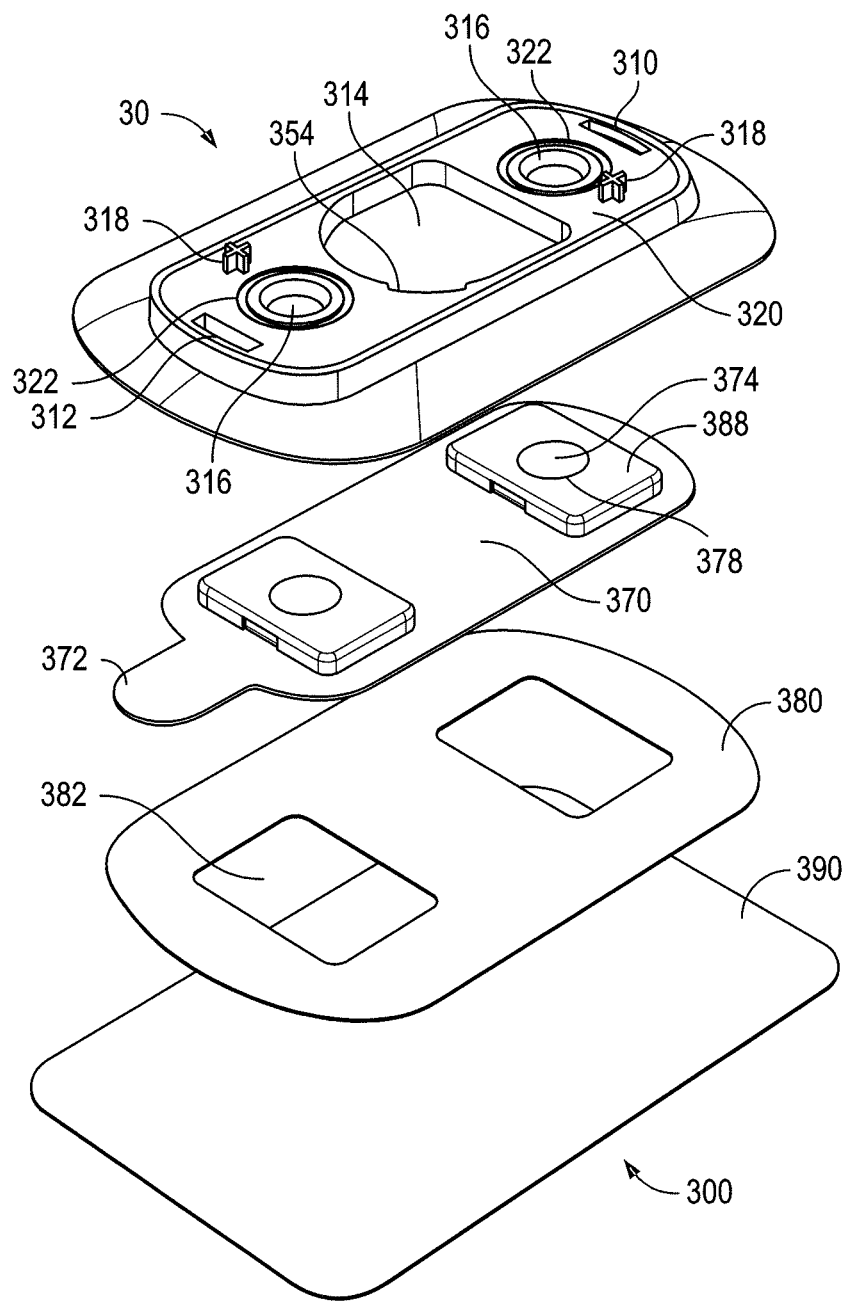
FIG. 4 shows an exploded perspective view of an exemplary reservoir module.

Another view of the reservoir module 30 appears in FIG. 4. In this view, the electrodes 374 are viewed through the apertures 378 in the reservoir compartments 388. Notable in FIG. 4 is the recess 314 has an indent 354, which is adapted to accept a complementary feature on the underside of an electrical module. This is one of many possible keying that may be provided for the device. In some embodiments, the recess 314 may receive the underside of a battery compartment in the electrical module; however the person skilled in the art will recognize that many such keying features are possible. One such keying feature may be the dimensions of the snap receptacles 310, 312 and the corresponding snaps, which permit assembly of the two modules in one configuration only. Other keying features could include the size and/or position of the electrical inputs 316 on the reservoir module 30 and the corresponding electrical outputs on the electrical module, the size and/or positions of the power-on posts 318, the complementary shapes of the reservoir module 30 and the electrical module 20.

Figure 5:
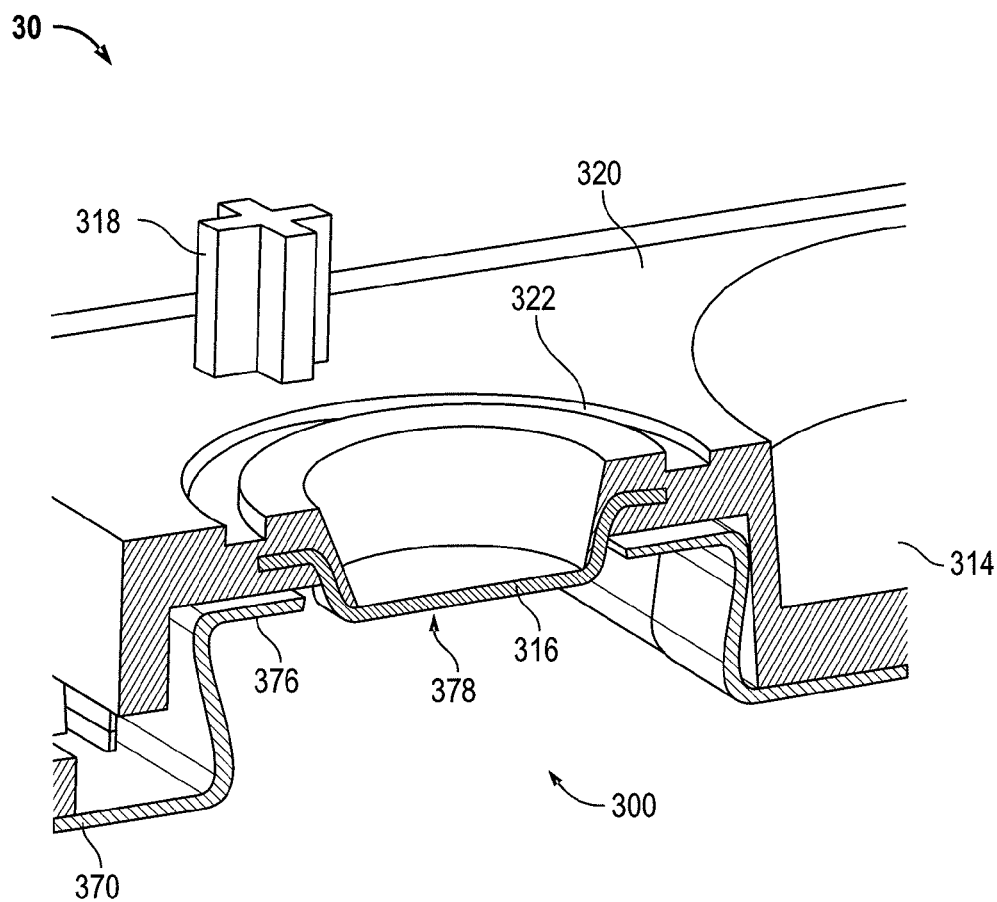
FIG. 5 is a cross-section perspective view of a reservoir contact.

FIG. 5 is a cross section perspective view of an input connector 316 on a reservoir module 30. Visible in this view are the upper surface 320 of the reservoir body 300. Circumscribing the input connector 316 is a seal 322. The seal 322 is configured to contact a corresponding seal on an electrical module to prevent ingress of contaminants upon assembly of the device. The contact 316 is in some embodiments advantageously a planar (flat or substantially flat) metallic contact. The contact may be essentially any conductive metal, such as copper, brass, nickel, stainless steel, gold, silver or a combination thereof. In some embodiments, the contact is gold or gold plated.

Also visible on the upper surface 320 of the reservoir module 30 is a power-on post 318 protruding from the surface 320. The lower portion of input connector 316 is configured to contact a reservoir (not pictured) through an aperture 378 in the reservoir compartment 388 in the electrode housing 370.

Additionally, part of the battery receptacle 314 may be seen in FIG. 5.

Figure 6:
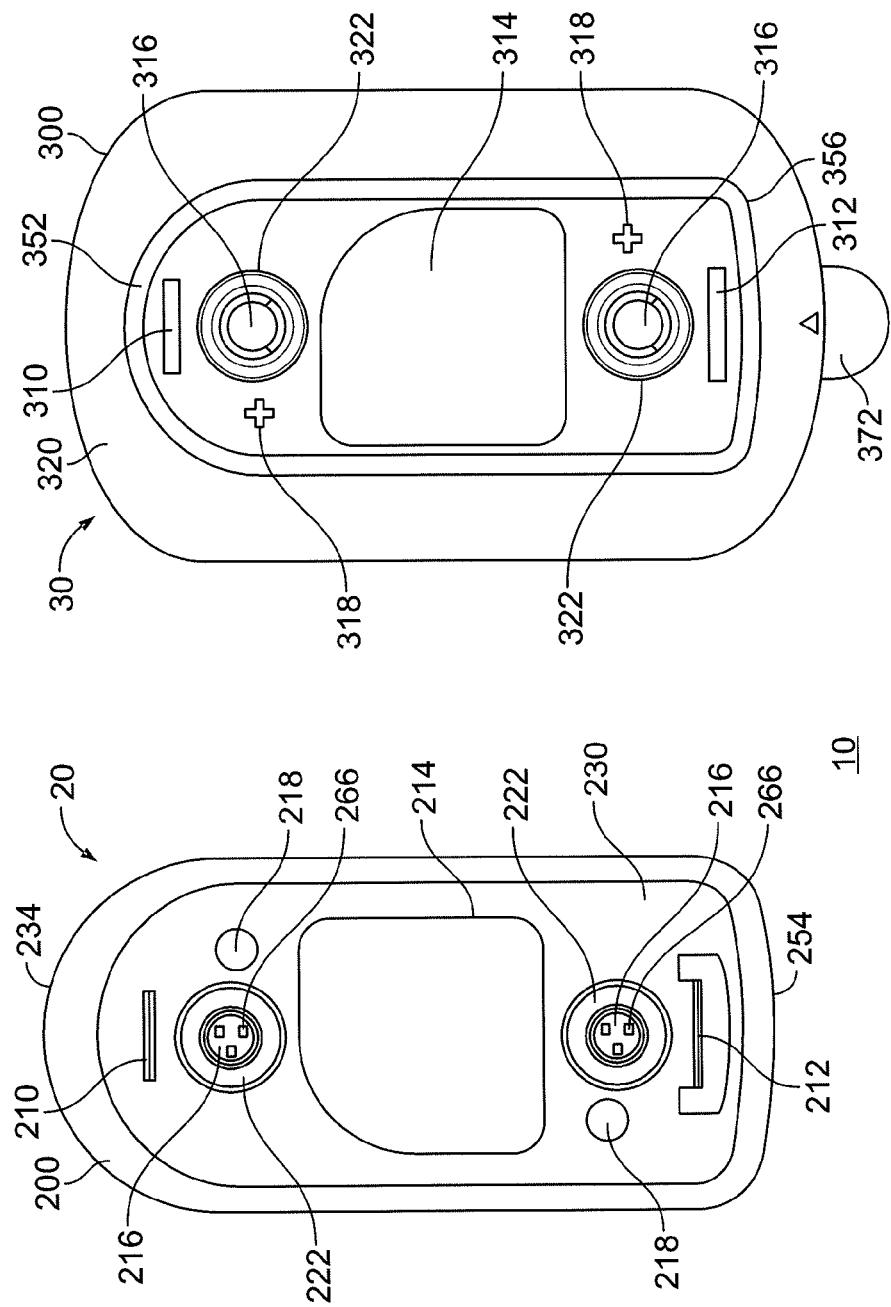
FIG. 6 shows a bottom view of an electrical module and a top view of a reservoir module.

FIG. 6 is another view of the two modules 20, 30 side by side. On the left side of FIG. 6 is the bottom side of the electrical module body 200; and on the right side is the top side of the reservoir module 30. The bottom surface 230 of electrical module body 200 has snaps 210, 212 protruding therefrom, which are sized and shaped to fit within the snap receptacles 310, 312 on the top of the reservoir module body 300. As discussed above, in some embodiments snaps 210 and 212 are of different size so that snap 210 will not fit within snap receptacle 312 and/or snap 212 will not fit within snap receptacle 310. This is one of several keying features that may be incorporated in the device 10. As an illustrative example, snap 212 cannot fit into 310, because snap 212 is larger than receptacle 310; but snap 210 can fit into receptacle 312, because it is the smaller snap and larger receptacle. In other embodiments, it is possible to size both snaps and receptacles so that the one snap/receptacle pair is larger in one dimension (e.g., horizontally), while the other snap/receptacle pair is larger in the other dimension (e.g., longitudinally). Another keying feature is the protrusion 214, which may house the battery or other component, and which is shaped to fit in one configuration within recess 314 only.

The snaps 210, 212 are at least in some embodiments one-way snaps, meaning that they are biased so as to fit within the receptacles 310, 312 in such a way that they are not easily removed, and in at least some preferred embodiments, are configured to break (or deform to the extent that they are no longer operable) if forced apart so that the modules 20, 30 cannot be reassembled to form a single unitary device. In some embodiments, such a feature is provided as an anti-abuse character to the device, such that the reservoir module 30 cannot be saved after use and employed with a different (or the same) electrical module 20.

The lower surface 230 of electrical module body 200 also has two electrical outputs 216, which are also referred to herein as output "hats", which in certain embodiments are have one or more bumps 266 protruding from the surface thereof. These hats 216 are circumscribed by hat seals 222. The hats 216 are configured to make contact with the input connectors 316 on the reservoir body 300. Additionally, the hat seals 222 are configured to contact and create an impermeable seal with the input seals 322. Advantageously the hat seals 222 are made of an elastomeric material that creates a contaminant-impermeable seal around the hats 216 and, when mated with the input connector seals 322, creates further contaminant-impermeable seals.

The power-on receptacles 218 are configured to receive input posts 318. In some embodiments, the power-on receptacles 218 are made of a deformable (e.g. elastomeric) material. In some such embodiments, the power-on posts 318 deform the power-on receptacles 218 so that they contact power-on contacts (described in more detail below) and move them to a closed position, thereby connecting the battery into the circuit. Once the two modules 20, 30 are snapped together, the posts maintain pressure on the power-on contacts through the receptacles 218 and keep the battery in the circuit.

While the hats 216 and input contacts 316 are depicted in FIG. 6 as being essentially the same size and symmetrically disposed along the longitudinal axis of the device 10, another keying feature may be introduced into the device by changing the relative size and/or position with respect to the longitudinal axis of the hats 216 and contacts 316, the power-on posts 318 and receptacles 218, etc.

Figure 7A:
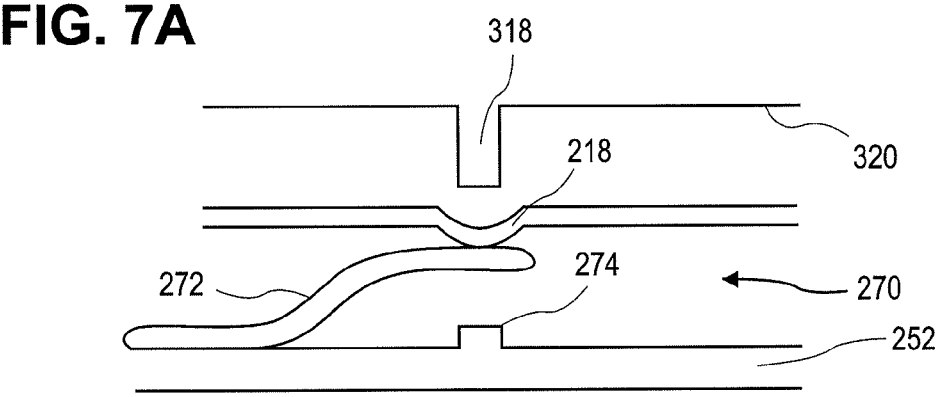
FIGS. 7A and 7B show cross-section views of a power-on connector when open (prior to actuation) and closed by a power-on post acting through a power-on receptacle.
Figure 7B:
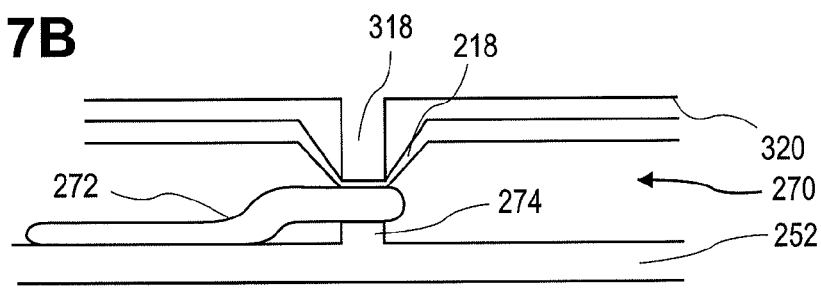

A cross section of one embodiment of a power-on switch 270 is depicted in FIGS. 7A and 7B. The power-on switch 270 comprises movable contact 272 and a stationary contact 274. Each of the movable contact 272 and the stationary contact 274 is connected to a portion of the circuitry on the printed circuit board (PCB) 252. In the open position depicted in FIG. 7A, the movable contact 272 is biased away from the stationary contact 274, whereas in the closed position depicted in FIG. 7B, the two contacts 272 and 274 are pressed together by the power-on post 318, which protrudes from the upper surface 320 of the reservoir module 30. The power-on post 318 acts through the flexible (elastomeric) power-on receptacle 218 to force the movable contact 272 down until it is in contact with the stationary contact 274. For the sake of visibility, the stationary contact 274 is shown elevated from the PCB 252; however, it will be understood that the stationary contact 274 need not be, and generally will not be, elevated from the PCB 252. In at least some embodiments, the stationary contact 274 will be an exposed metal trace on the surface of the PCB 252, though other configurations are also possible. The stationary contact 272 is manufactured from a suitably springy metal, such as a copper alloy, which is biased to remain in the first, open position unless acted on by the power-on post 318. The receptacle 218 may resemble a dome when viewed from the side of facing the contacts 272, 274, and is at least in some embodiments formed of a suitable elastomeric substance that permits the power-on post 318 to deform it without rupturing the seal. In some embodiments, the receptacle 218 may also be planar or may be domed in the opposite direction. In at least some embodiments, the receptacle 218 provides a contaminant-tight seal between the external and internal parts of the electrical module 20.

Figure 8:
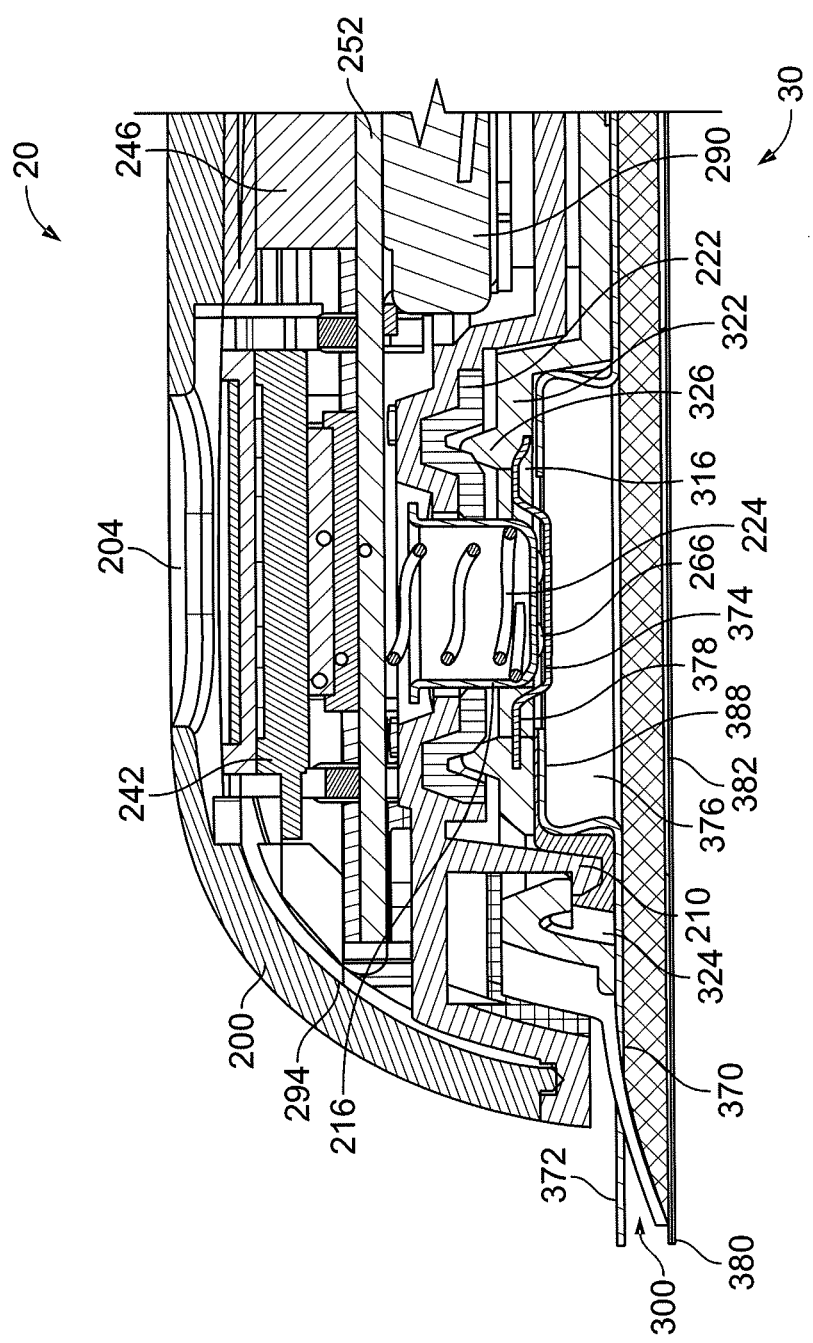
FIG. 8 shows a cross-section view of an output from the electrical module making contact with an input connector on the reservoir module.

FIG. 8 shows a cross section of a part of a device 10 in an assembled state. The device 10 comprises the upper electrical module 20, comprising an upper body 200, and the reservoir module 30, comprising reservoir body 300, which are shown in this cross section view as combined. Parts of the electrical module 20 that are visible in this cross section view include the electrical module body 200, which contains a sound transducer 246, an LCD 204, controller 242, and battery 290, all of which are on the printed circuit board (PCB) 252. A flex circuit 294 provides a connection between the PCB 252 and the LCD 204. Also visible are the contact hat 216, which has bumps 266, and snap 210. As can be seen, the contact hat 216 is biased toward the reservoir module 30 by a coil spring 224, which fits within the contact hat 216 and exerts a force through the contact hat 216 to press the contact hat 216 against the input connector 316 of the reservoir module 30. The hat 216 is circumscribed by a hat seal 222, which contacts the hat 216 through its full length of travel. In at least some embodiments, this hat seal 222 is an elastomeric seal that provides a contaminant-tight fit between the hat seal 222 and the hat 216, whereby the electrical module 20 is sealed against contaminants such as particles and fluids (e.g. humidity) in the environment.

The reservoir module 30 includes a reservoir 376 and an electrode 374 within the reservoir compartment 388 in the electrode housing 370, which also has an electrode housing tab 372. In the assembled state, the snap 210 catches on the ledge 324 of the snap receptacle 310. At least in some embodiments, the snap 210 is made of a resilient polymer and is biased to maintain contact with the ledge 324 so that the two modules 20, 30 cannot be easily separated. In some preferred embodiments, the snap 210 is configured so that if the two modules 20, 30 are separated, the snap 210 (and/or the ledge 324) will break (or deform to the extent that they are no longer operable) and thereafter be unable to couple the two modules together.

Also depicted in this view is an input connector seal 322, which in this illustration forms a ridge 326 (input connector seal ridge) that circumscribes the input connector 316. When the two modules 20, 30 are assembled, this input connector seal ridge 326 contacts and presses into the elastomeric hat seal 222, thereby preventing ingress of contaminants, such as particulates and liquids, into the space containing the output contact hat 216 and the input contact 316.

The hat 216 projects through the aperture 378 in the reservoir compartments 388. At least the bumps 266 on the hat 216 contact the input connector 316 to provide electrical contact between the electrical module 20 and the reservoir module 30. The spring 224 provides mechanical bias to force the bumps 266 to maintain contact with the input connector 316. Although the hat 216 is shown being biased by a coil spring 224, the person having skill in the art will recognize that other springs and spring-like devices can be used within the scope of the device described herein. For example, and without limitation, the coil spring 224 could be replaced by a beam spring or similar device.

Figure 9:
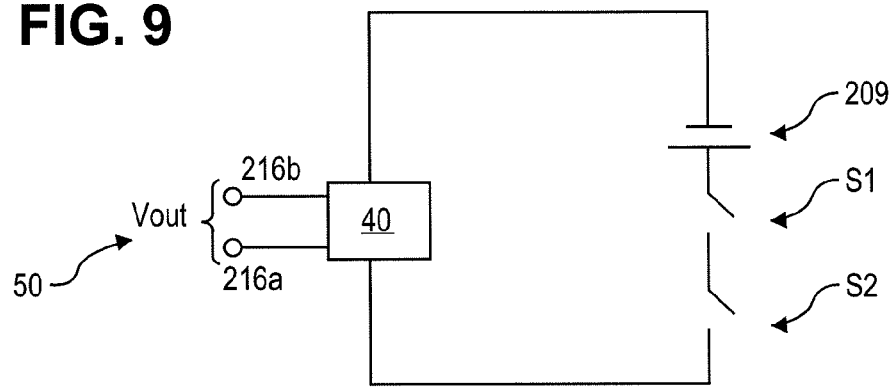
FIG. 9 is a circuit diagram for electronics within an electrical module of the device described herein.

As can be seen in FIG. 9, which is a high level schematic diagram of the electronics 50 within the electrical module 20, the electronics 50 can be envisioned as including circuitry 40 (which includes the controller, various indicators, etc.) connected to the battery 290 through power-on switches S1 and S2 (which correspond to power-on switch 270 in FIGS. 7A, 7B). The circuitry 40 controls delivery of voltage Vout through the outputs 216a, 216b, which connect to corresponding inputs on the reservoir module. It is to be understood that, although the configuration of power-on switches S1 and S2 shown in FIGS. 7A and 7B is considered to provide certain advantages, such as ease of operation and manufacture, other configurations of switches may be employed within the scope of the device described herein. Such switches may include slides switches that are mechanically biased toward the open position, which may be pushed to the closed position by a power-on post or similar actuator. As can be seen in this figure, the circuit 50 comprising the battery 209 and the rest of the circuitry 40 is only completed if both S1 and S2 are both held closed. Prior to S1 and S2 being closed, e.g. through the mechanical action of power-on posts, the battery 290 is isolated from the circuitry 40, as the circuit is open and does not allow current to flow through it. As mentioned before, this reduces battery drain prior to use and greatly reduces corrosion, as the circuitry has no power supply, and thus no extrinsic charge, applied to it. Also, if during handling prior to use one of the switches happens to close, e.g. for a brief period of time, the device will not power on. At least in some embodiments, it is considered advantageous for the controller to detect spurious short-lived closing of both switches S1 and S2 in order to account for occasional, accidental closing of the switches before use. Also, as discussed above, it is considered advantageous in some embodiments that the two switches S1 and S2 be physically and/or electrically remote from one another. Separation of the two switches reduces the likelihood that something that causes one of the switches to malfunction (e.g. close, whether permanently, reversibly or intermittently) will not also affect the other switch. Additionally or alternatively, the two switches may be located on two different sides of the battery or on the same side of the battery. Thus, while in FIG. 9 the switches S1, S2 are depicted on the positive (+) side of the battery 290, one or both could be located on the other side of the battery. Thus, 1, 2, 3 or more switches may be located on one (positive or negative) side of the battery and 0, 1, 2, 3 or more switches may be located on the other (negative or positive) side of the battery. Physical separation of the two switches may be from 0.1 cm to several cm, and in some embodiments at least 0.5 cm.

Also apparent is FIG. 9 is that the switches S1, S2 are remote from the outputs 216a, 216b. Thus, the outputs from the electrical module to the reservoir module are separated from the switches S1, S2. Though in some preferred embodiments the closing of switches S1, S2 occurs as a result of the same action that connects the outputs 216a, 216b to the corresponding inputs on the reservoir module, the switches S1, S2 are remote from the outputs 216a, 216b. This allows switches S1, S2 to be entirely internal to the electrical module, and in some embodiments to be sealed against ingress of contaminants, such as water (including vapor) and/or particulates.

Figure 10:
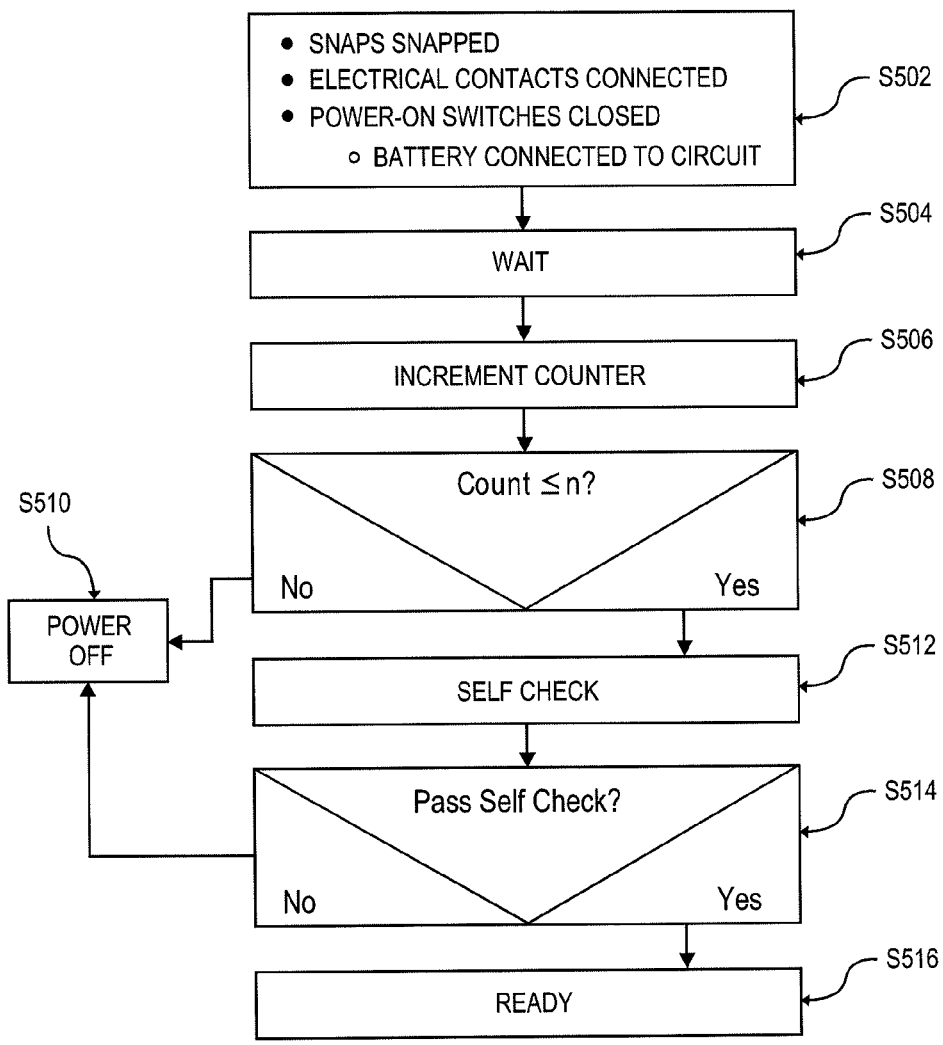
FIG. 10 is a flow chart showing a power-on sequence of a device as described herein.
Figure 11:
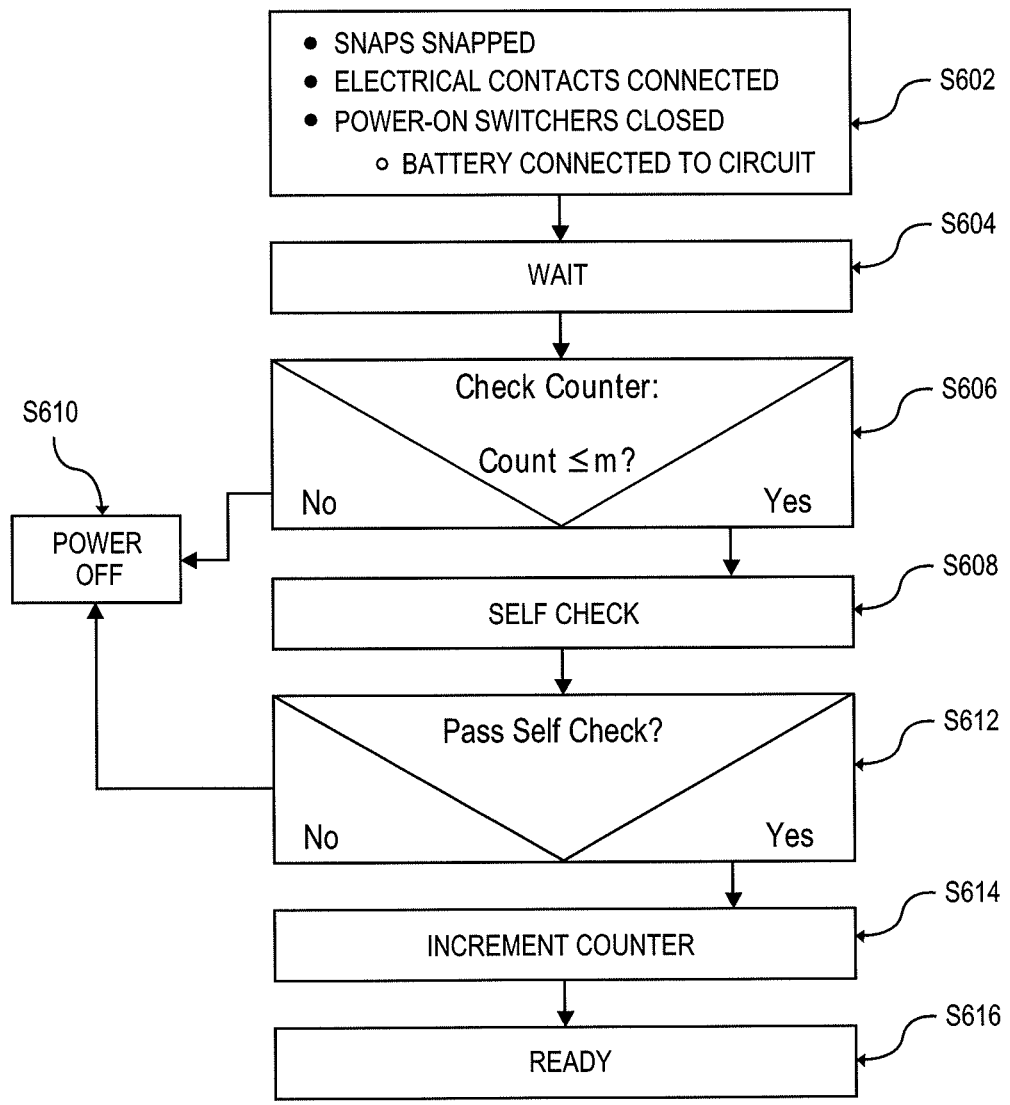
FIG. 11 is a second flow chart showing an alternative power-on sequence of a device as described herein.

FIGS. 10 and 11 provide two alternative power-on sequences for a device 10 according as described herein. The first alternative shows that in the first step, S502, four events occur all at once in a single action by the user: the snaps are snapped into their respective receptacles; the output and input contacts are mated to provide electrical contact between the reservoirs in the reservoir module and the circuitry in the electrical module; the power-on posts close the power-on switches in the electrical module; and the battery is thereby connected into the circuit and begins providing power to the circuitry. In step S504 the controller waits a minimum period of time (e.g. 10-500 ms) before proceeding to the next step. In some embodiments, S504 is eliminated from the power-on sequence. In embodiments in which S504 is included in the power-on sequence, if the controller fails to maintain power for a predetermined minimum period of time, that is, e.g. power is lost during this timeframe, the timer resets to zero. Presuming that power is maintained through the time period of step S504, the controller then increments the power-on counter by 1 in step S506. In step S508, the controller then checks the number of counts on the power-on counter, and if it is less than or equal to a certain predetermined number (in this example 2, presuming that the counter had been set to 1 by an in-factory test, though other values are possible) the controller proceeds to step S510, which includes a self-check. If, however, the count is greater than the predetermined number, then the controller initiates step S516, which includes a power off sequence, which may include sending an error message to an LCD display, activating an LED indicator and/or sounding an audible alarm. If the count is less than or equal to the predetermined number, the controller initiates step S510. After the self-check of S510 is completed, the controller determines whether the circuitry has passed the self-check, and if not, it initiates step S516. If the circuitry passes the self-test check, the controller then initiates S512, which may include signaling the user that the device is ready (e.g. through the LCD, LED and/or sound transducer). The device is then ready to be applied to the body of a patient and operated normally, e.g. as described in U.S. Pat. No. 6,216,033 B1, which is incorporated herein by reference in its entirety.

A second alternative in FIG. 11 shows that in the first step, S602, four events occur all at once in a single action by the user: the snaps are snapped into their respective receptacles; the output and input contacts are mated to provide electrical contact between the reservoirs in the reservoir module and the circuitry in the electrical module; the power-on posts close the power-on switches in the electrical module; and the battery 290 is thereby connected into the circuit and begins providing potential to the circuitry. In step S604 the controller waits a minimum period of time (e.g. 10-500 ms) before proceeding to the next step. If the controller fails to maintain power for this period of time, that is, power is lost during this timeframe, the timer resets to zero. Presuming that power is maintained through the time period of step S604, the controller then checks the number of counts on the power-on counter in S606, and if it is less than or equal to a certain predetermined number (in this example 1, presuming that the counter had been set to 1 by an in-factory test, though other values are possible) the controller proceeds to step S610, which includes a self-check. If, however, the count is greater than the predetermined number, then the controller initiates step S616, which includes a power off sequence, which may include sending an error message to an LCD display, activating an LED indicator and/or sounding an audible alarm. If the count is less than or equal to the predetermined number, the controller initiates step S610. After the self-check of S610 is completed, the controller determines whether the circuitry has passed the self-check, and if not, it initiates step S616. If the circuitry passes the self-test check, the controller then initiates S612, which includes incrementing the counter by 1. The controller then initiates S614, which may include signaling the user that the device is ready (e.g. through the LCD, LED and/or sound transducer). The device is then ready to be applied to the body of a patient and operated normally, e.g. as described in U.S. Pat. No. 6,216,033 B1, which is incorporated herein by reference in its entirety.

Briefly described, the device is applied to the surface of a patient's skin. The patient or a healthcare professional may then press the button 202 (see, e.g., FIGS. 2A, 2B, and 3). In some embodiments, the device is configured to require the patient or healthcare professional to press the button twice within a predetermined timeframe in order to prevent accidental or spurious administration of the therapeutic agent. Provided the patient or healthcare professional properly presses the button 202, the device 10 then begins administering the therapeutic agent to the patient. In between the doses, the device may enter a "Ready" mode during which the delivery is "off" even though the device is powered on. While in the Ready mode, the device may also perform a number of self-test including the off-current self-test described above. If the user presses the button to receive another dose, the device may first perform one or more self-tests (including the off-current self-test) before delivering the dose (entering the activated state and delivering dosage by passing current between the anode and cathode). Once a predetermined number of doses have been administered and/or a predetermined period of time has elapsed since the device was powered on, the device initiates a power off sequence, which may include sending a power off signal to the user through an LCD display, an LED and/or an audio transducer. See especially the claims of U.S. Pat. No. 6,216,033 B1, which are incorporated herein by reference.

The person skilled in the art will recognize that other alternative power-on sequences may be employed. For example, the controller may increment the counter immediately after the counter check in the process outlined in FIG. 10 or 11.

The reservoir of the electrotransport delivery devices generally contain a gel matrix, with the drug solution uniformly dispersed in at least one of the reservoirs. Other types of reservoirs such as membrane confined reservoirs are possible and contemplated. The application of the present invention is not limited by the type of reservoir used. Gel reservoirs are described, e.g., in U.S. Pat. Nos. 6,039,977 and 6,181,963, which are incorporated by reference herein in their entireties. Suitable polymers for the gel matrix can comprise essentially any synthetic and/or naturally occurring polymeric materials suitable for making gels. A polar nature is preferred when the active agent is polar and/or capable of ionization, so as to enhance agent solubility. Optionally, the gel matrix can be water swellable nonionic material.

Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly(allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

Incorporation of the drug solution into the gel matrix in a reservoir can be done in any number of ways, i.e., by imbibing the solution into the reservoir matrix, by admixing the drug solution with the matrix material prior to hydrogel formation, or the like. In additional embodiments, the drug reservoir may optionally contain additional components, such as additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art. Such materials can be included by on skilled in the art.

The drug reservoir can be formed of any material as known in the prior art suitable for making drug reservoirs. The reservoir formulation for transdermally delivering cationic drugs by electrotransport is preferably composed of an aqueous solution of a water-soluble salt, such as HCl or citrate salts of a cationic drug, such as fentanyl or sufentanil. More preferably, the aqueous solution is contained within a hydrophilic polymer matrix such as a hydrogel matrix. The drug salt is preferably present in an amount sufficient to deliver an effective dose by electrotransport over a delivery period of up to about 20 minutes, to achieve a systemic effect. The drug salt typically includes about 0.05 to 20 wt % of the donor reservoir formulation (including the weight of the polymeric matrix) on a fully hydrated basis, and more preferably about 0.1 to 10 wt % of the donor reservoir formulation on a fully hydrated basis. In one embodiment the drug reservoir formulation includes at least 30 wt % water during transdermal delivery of the drug. Delivery of fentanyl and sufentanil has been described in U.S. Pat. No. 6,171,294, which is incorporated by reference herein. The parameter such as concentration, rate, current, etc. as described in U.S. Pat. No. 6,171,294 can be similarly employed here, since the electronics and reservoirs of the present invention can be made to be substantially similar to those in U.S. Pat. No. 6,171,294.

The drug reservoir containing hydrogel can suitably be made of any number of materials but preferably is composed of a hydrophilic polymeric material, preferably one that is polar in nature so as to enhance the drug stability. Suitable polar polymers for the hydrogel matrix include a variety of synthetic and naturally occurring polymeric materials. A preferred hydrogel formulation contains a suitable hydrophilic polymer, a buffer, a humectant, a thickener, water and a water soluble drug salt (e.g. HCl salt of a cationic drug). A preferred hydrophilic polymer matrix is polyvinyl alcohol such as a washed and fully hydrolyzed polyvinyl alcohol (PVOH), e.g. MOWIOL 66-100 commercially available from Hoechst Aktiengesellschaft. A suitable buffer is an ion exchange resin which is a copolymer of methacrylic acid and divinylbenzene in both an acid and salt form. One example of such a buffer is a mixture of POLACRILIN (the copolymer of methacrylic acid and divinyl benzene available from Rohm & Haas, Philadelphia, Pa.) and the potassium salt thereof. A mixture of the acid and potassium salt forms of POLACRLIN functions as a polymeric buffer to adjust the pH of the hydrogel to about pH 6. Use of a humectant in the hydrogel formulation is beneficial to inhibit the loss of moisture from the hydrogel. An example of a suitable humectant is guar gum. Thickeners are also beneficial in a hydrogel formulation. For example, a polyvinyl alcohol thickener such as hydroxypropyl methylcellulose (e.g. METHOCEL K100 MP available from Dow Chemical, Midland, Mich.) aids in modifying the rheology of a hot polymer solution as it is dispensed into a mold or cavity. The hydroxypropyl methylcellulose increases in viscosity on cooling and significantly reduces the propensity of a cooled polymer solution to overfill the mold or cavity.

Polyvinyl alcohol hydrogels can be prepared, for example, as described in U.S. Pat. No. 6,039,977. The weight percentage of the polyvinyl alcohol used to prepare gel matrices for the reservoirs of the electrotransport delivery devices, in certain embodiments can be about 10% to about 30%, preferably about 15% to about 25%, and more preferably about 19%. Preferably, for ease of processing and application, the gel matrix has a viscosity of from about 1,000 to about 200,000 poise, preferably from about 5,000 to about 50,000 poise. In certain preferred embodiments, the drug-containing hydrogel formulation includes about 10 to 15 wt % polyvinyl alcohol, 0.1 to 0.4 wt % resin buffer, and about 1 to 30 wt %, preferably 1 to 2 wt % drug. The remainder is water and ingredients such as humectants, thickeners, etc. The polyvinyl alcohol (PVOH)-based hydrogel formulation is prepared by mixing all materials, including the drug, in a single vessel at elevated temperatures of about 90 degree C. to 95 degree C. for at least about 0.5 hour. The hot mix is then poured into foam molds and stored at freezing temperature of about −35 degree C. overnight to cross-link the PVOH. Upon warming to ambient temperature, a tough elastomeric gel is obtained suitable for ionic drug electrotransport.

A variety of drugs can be delivered by electrotransport devices. In certain embodiments, the drug is a narcotic analgesic agent and is preferably selected from the group consisting of fentanyl and related molecules such as remifentanil, sufentanil, alfentanil, lofentanil, carfentanil, trefentanil as well as simple fentanyl derivatives such as alpha-methyl fentanyl, 3-methyl fentanyl and 4-methyl fentanyl, and other compounds presenting narcotic analgesic activity such as alphaprodine, anileridine, benzylmorphine, beta-promedol, bezitramide, buprenorphine, butorphanol, clonitazene, codeine, desomorphine, dextromoramide, dezocine, diampromide, dihydrocodeine, dihydrocodeinone enol acetate, dihydromorphine, dimenoxadol, dimeheptanol, dimethylthiambutene, dioxaphetyl butyrate, dipipanone, eptazocine, ethylmethylthiambutene, ethylmorphine, etonitazene, etorphine, hydrocodone, hydromorphone, hydroxypethidine, isomethadone, ketobemidone, levorphanol, mepethidine, meptazinol, metazocine, methadone, methadyl acetate, metopon, morphine, heroin, myrophine, nalbuphine, nicomorphine, norlevorphanol, normorphine, norpipanone, oxycodone, oxymorphone, pentazocine, phenadoxone, phenazocine, phenoperidine, piminodine, piritramide, proheptazine, promedol, properidine, propiram, propoxyphene, and tilidine.

Some ionic drugs are polypeptides, proteins, hormones, or derivatives, analogs, mimics thereof. For example, insulin or mimics are ionic drugs that can be driven by electrical force in electrotransport.

For more effective delivery by electrotransport salts of certain pharmaceutical analgesic agents are preferably included in the drug reservoir. Suitable salts of cationic drugs, such as narcotic analgesic agents, include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, .beta.-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate. The more preferred salt is chloride.

A counterion is present in the drug reservoir in amounts necessary to neutralize the positive charge present on the cationic drug, e.g. narcotic analgesic agent, at the pH of the formulation. Excess of counterion (as the free acid or as a salt) can be added to the reservoir in order to control pH and to provide adequate buffering capacity. In one embodiment of the invention, the drug reservoir includes at least one buffer for controlling the pH in the drug reservoir. Suitable buffering systems are known in the art.

The device described herein is also applicable where the drug is an anionic drug. In this case, the drug is held in the cathodic reservoir (the negative pole) and the anoidic reservoir would hold the counterion. A number of drugs are anionic, such as cromolyn (antiasthmatic), indomethacin (anti-inflammatory), ketoprofen (anti-inflammatory) and ketorolac tromethamine (NSAID and analgesic activity), and certain biologics such as certain protein or polypeptides.

Although the device and systems for drug delivery including an off-current self-test (and therefore an off-current module to perform the self-test) may be or include two-part drug delivery devices as descried above, the off-current module may be included as part of virtually any drug delivery system having a powered on, but delivery-off (e.g., "Ready") mode in which drug is not to be delivered until appropriately triggered. Thus one-part, unitary drug delivery devices are also contemplated.

Any of the systems and devices describe herein, including a two-part system as exemplified may include logic for controlling the self-tests, including the off-current (aka anode-cathode voltage difference) self-test. Described in Example 2 below, and accompanying figures, is one variation of a system and control logic to be implemented on the system, including an off-current self-test. This exemplary logic includes an off-current module, and may be implemented on the two-part system described in Example 1, above.

Example 2

Control Logic

In one example, a system/device including an off-current control module configured to include an off-current self-test may include a processor or other controller executing control logic. For convenience, this control logic is referred to herein as software, however it should be understood that it may include hardware, firmware, or the like, in addition to software.

The following acronyms used in this example are defined below:

| Term | Definition |
| --- | --- |
| ITSIC | ASIC designed and produced for/by this example |
| ASIC | Application-Specific Integrated Circuit |
| IONSYS ™ | Fentanyl Iontophoretic Transdermal System |
| ITSIC | Specific Integrated Circuit (formerly called ALZIC) for this example |
| JTAG | (Joint Test Action Group) An interface to the ITSIC that allows access and control by external equipment |
| Nibble | Half of an 8-bit byte. Four bits aligned on bit zero or bit four of an 8-bit byte |
| Syndrome Bit | Hamming Code parity bit |
| TDI | Technical Design Input |
| UML | Unified Modeling Language |

In this example, the software (control logic) described herein may be run on the ITSIC ASIC, which contains a CAST R80515 CPU core. In addition to the core, the ITSIC contains peripherals for interfacing with input/output devices including buttons, LEDs, an LCD, and a piezo transducer. The ITSIC also includes a high-voltage boost converter, a current source, and an analog-to-digital converter (ADC).

The exemplary CAST R80515 core operates at 32 kHz and takes between one and six cycles to execute each instruction. This equates to execution times ranging from 31.25 to 187.5 μs is per instruction. The ITSIC contains 256 bytes of RAM, of which 32 bytes are reserved for core registers, 1024 bytes of non-volatile storage in the form of EEPROM arranged in 64-bit pages, and 16 KB of ROM for program memory. The ITSIC can execute code from program memory in internal ROM, or from external EEPROM. The transfer of execution from internal ROM to external EEPROM is controlled by a hardware register setting that may be configured via JTAG or by software.

Figure 12:
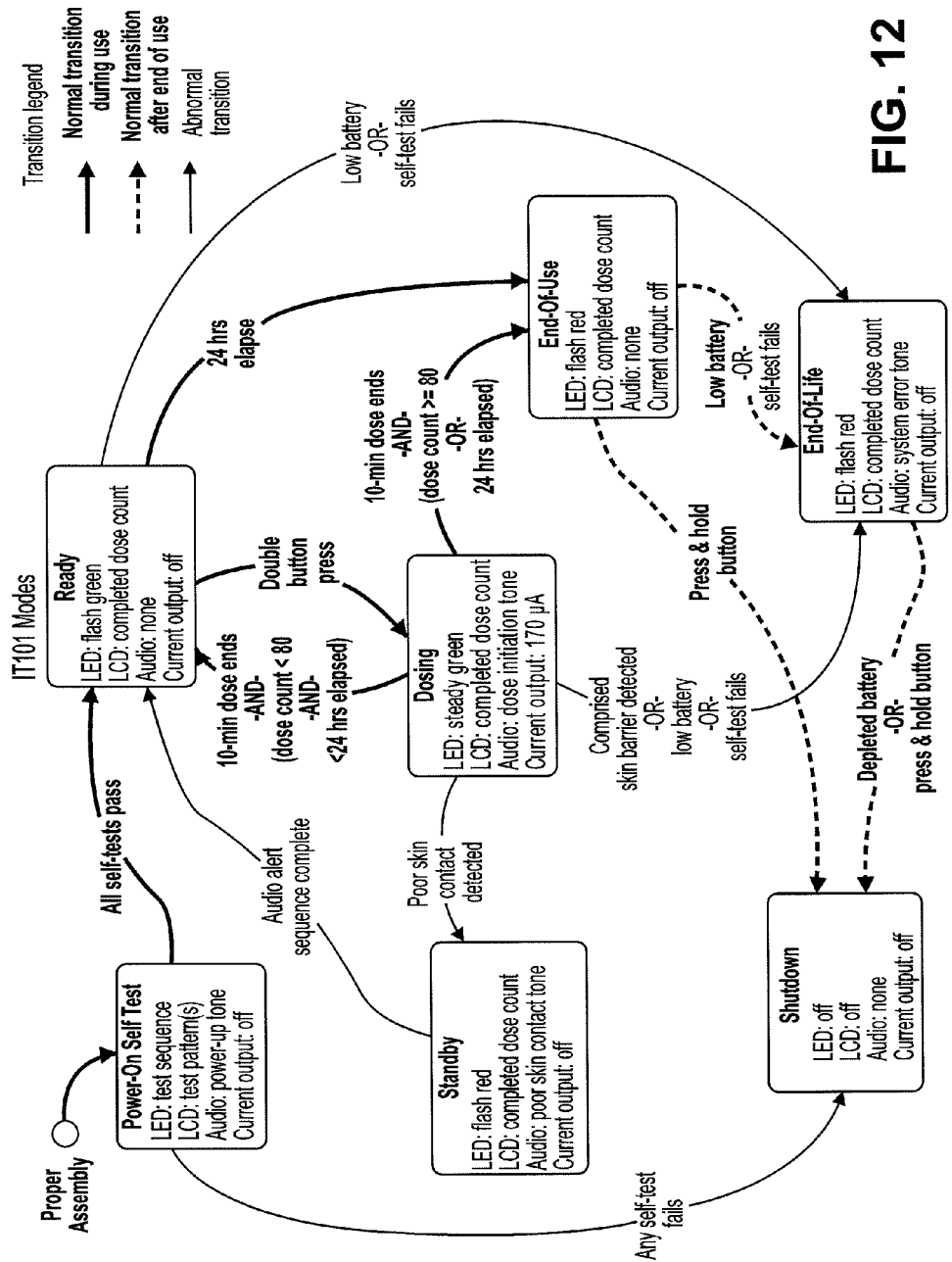
FIG. 12 is a diagram showing the user mode diagram for one exemplary embodiment of a system including an off-current self-test module.

The IT101 may operate in one of seven modes, determined by user input, defined operational parameters, and device internal status. FIG. 12 shows the behavior of each mode and the transitions between modes.

Figure 13:
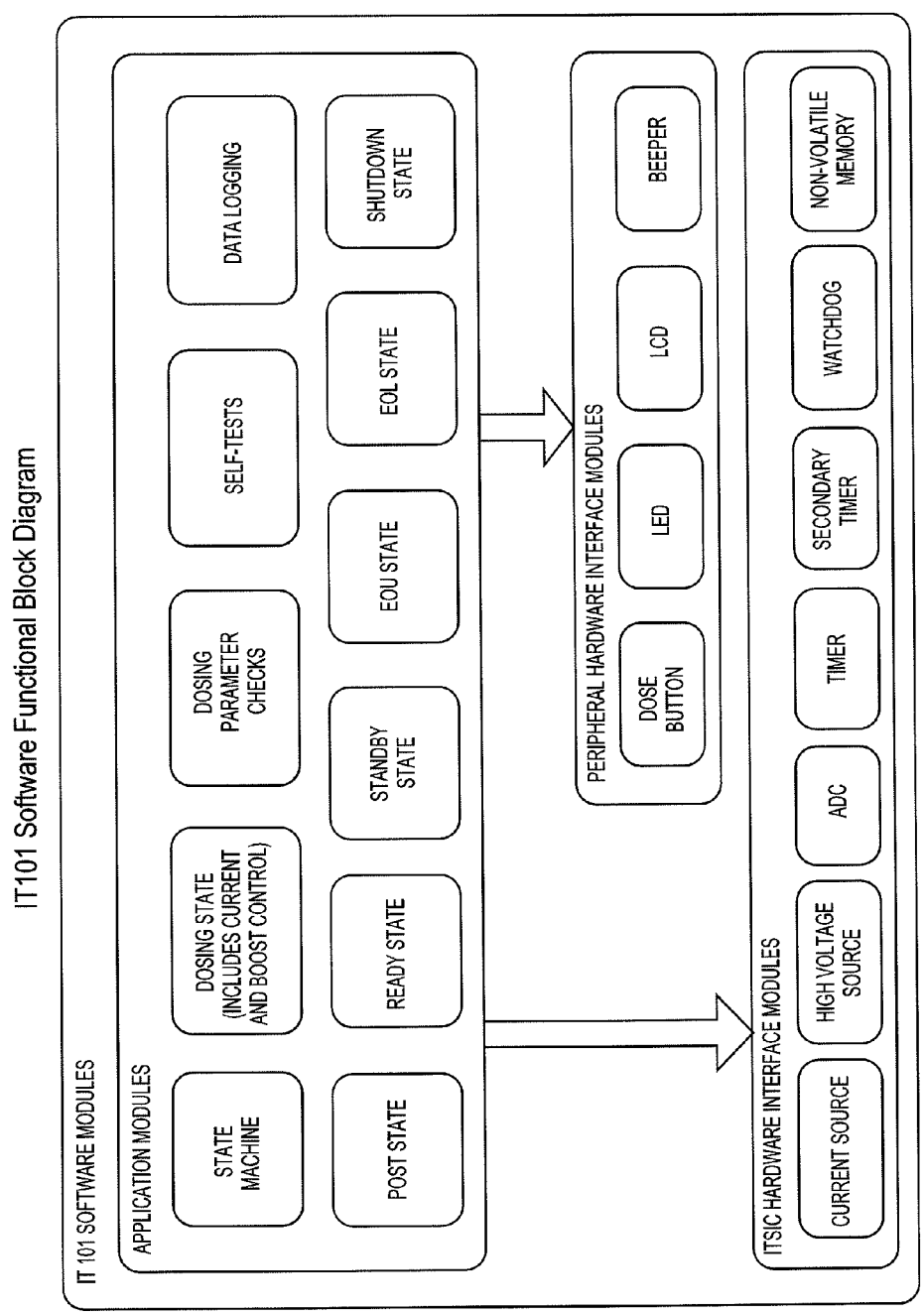
FIG. 13 shows an example of a software block diagram for the example of FIG. 12.

FIG. 13 shows the high-level decomposition of the software into functional blocks. The software architecture in this example is modular and layered, with low-level driver modules encapsulating and providing an interface to electronic hardware, while higher-level application modules utilize drivers to provide device functionality to the user. Lower-layer modules are independent of modules in layers above them.

Figure 14:
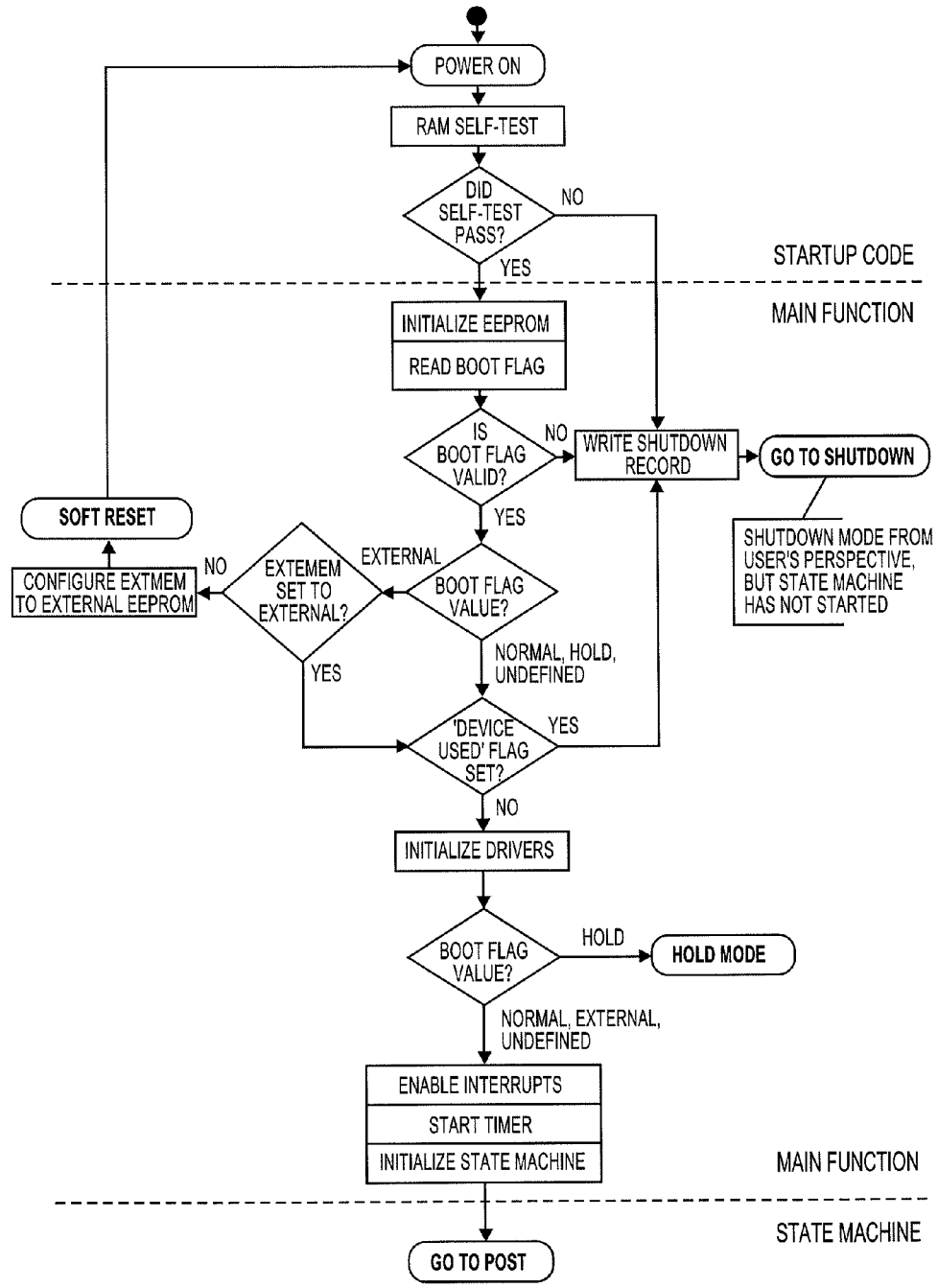
FIG. 14 illustrates one variation a procedure for system initialization.

Before entering the state machine, the software goes through an initialization routine. This routine includes checking the RAM and EEPROM for corruption, checking the boot mode, and initializing the drivers. More details of this initialization can be seen in FIG. 14.

The ITSIC supports execution from either internal Mask ROM or an external EEPROM. The default configuration is execution from ROM. In addition, the software includes a Hold Mode which initializes the system then enters an infinite loop to allow external control via the JTAG lines. Hold mode does not service the watchdog timer, so if external control isn't asserted prior to the first expiration of the watchdog, the watchdog will reset the system. The boot mode of the system is determined by the boot flag in NVM.

During system initialization, the EEPROM is initialized and the first page is checked for data integrity. If the boot flag value is not corrupt, the value is read from EEPROM.

If the flag is set to Normal, the software continues to run from ROM. If the flag is set to External, the EXTMEM register is set by software, which resets the CPU and subsequently boots from external EEPROM. If the flag is set to Hold, the drivers are first initialized, and then the software enters Hold Mode.

Processing of tasks in the system may be periodic and synchronized with a system tick occurring every eight milliseconds. The system tick function is provided by the Timer driver, using a periodic hardware interrupt to produce the tick. The main loop simply waits for the system tick to occur, then calls the appropriate processing functions for the Timer driver and the state machine.

The Timer processing function updates any active timers, such as those for dose time and system lifetime. The state machine processing function dispatches processing to the currently-active state, which then executes its periodic tasks. Periodic tasks may be scheduled to run as frequently as every 8 ms, or with any period that is an integer multiple of 8 ms, up to 2.048 seconds. The upper limit on the period is fixed by rollover of the 8-bit system tick counter. The Timer driver provides functions to facilitate periodic execution at various rates. To reduce demands on the processor core, tasks may be scheduled to run at rates no faster than necessary.

There is a single thread of execution that executes tasks in a non-preemptive, run-to-completion model. The active task must complete before the next task can run, so no task is allowed to wait for an extended period for an event to occur. If execution of a particular task runs past the scheduled time for one or more other tasks, the delayed task(s) will be executed in order, upon completion of the delaying task. Execution of all periodic processing tasks will generally take longer than the duration of a single system tick. Normal scheduling will continue on the next system tick.

Figure 15:
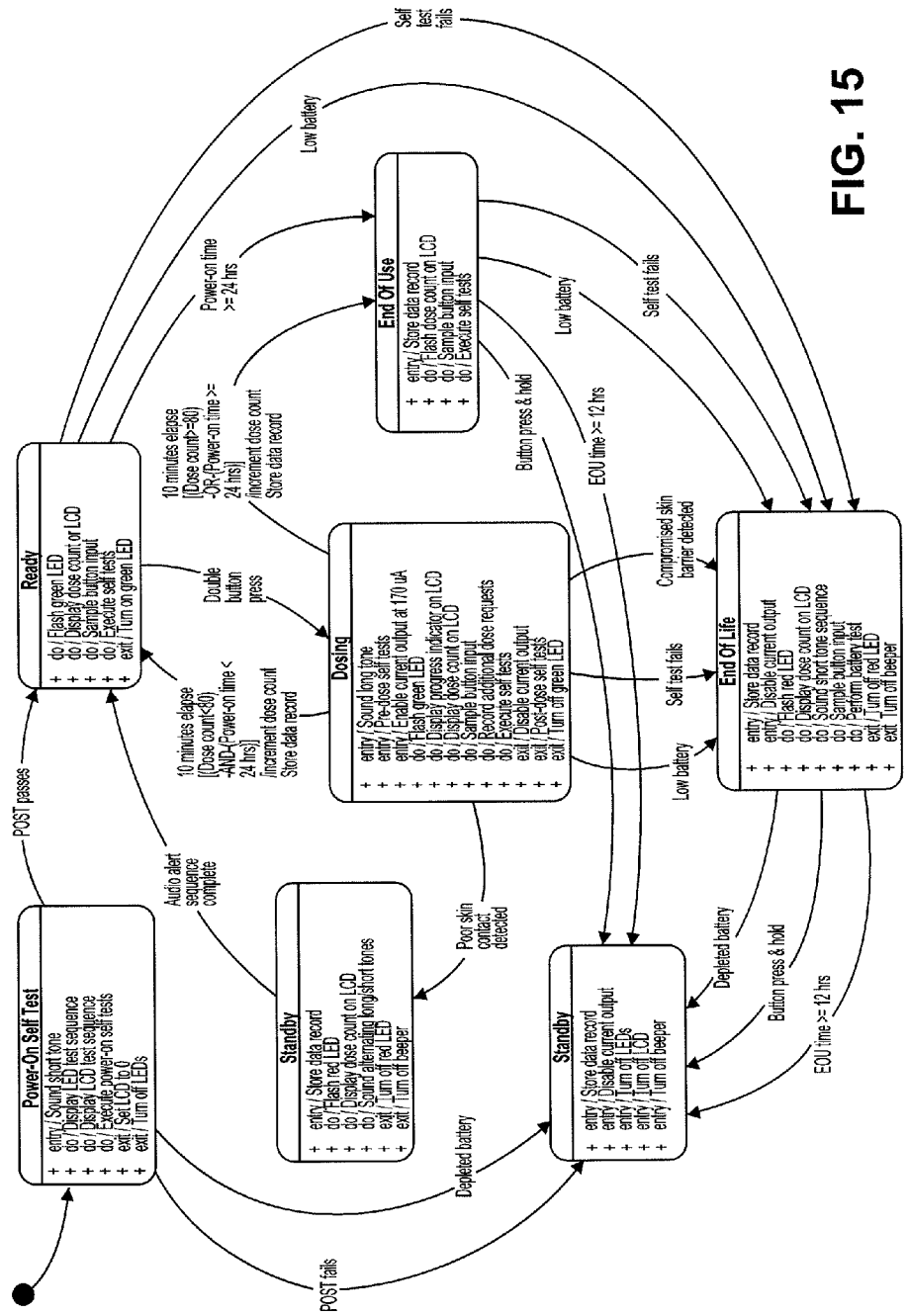
FIG. 15 shows a software state chart for the Example of FIG. 12.
Figure 16:
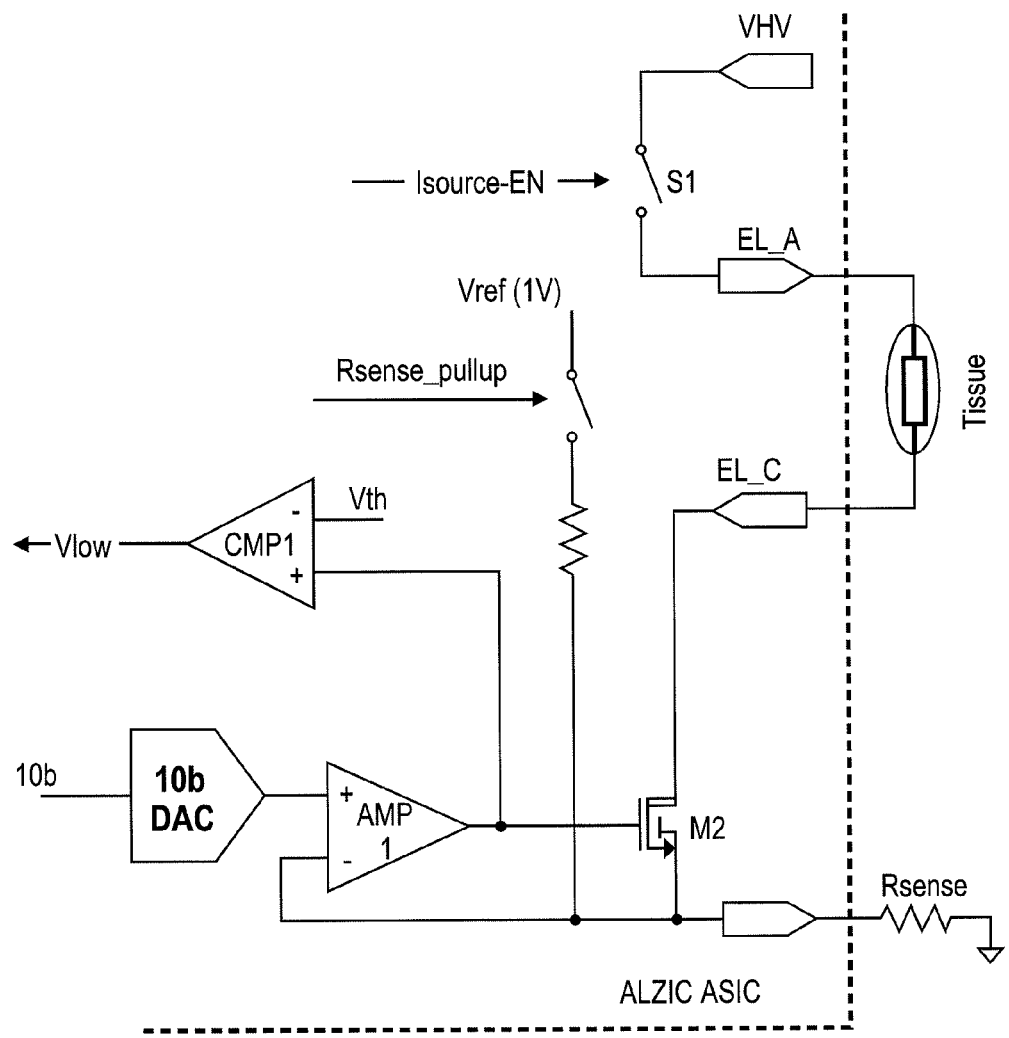
FIG. 16 is an exemplary diagram of a current control circuit for one variation of a drug delivery device.

The software in this example operates as a finite state machine, the behavior of which is defined in the UML state chart shown in FIG. 15. The state machine is implemented with state processing and transitions managed centrally by the StateMachine module. Each state has entry and exit functions, as well as a processing function. The current state of the system is stored in a single private variable within the StateMachine module.

Each time a system tick occurs, the main loop calls the state machine processing function, which in turn calls the processing function for the current state. If processing of the current state results in a transition, the processing function returns a reference to the new state. The state machine then calls the exit function for the current state, changes the state variable, then calls the entry function for the new state. This assures that the state of the system remains consistent at all times, with guaranteed state entry and exit actions performed in the correct order. If a state's processing function does not result in a transition, it returns null, and no state change takes place.

Each state contains its own list of periodic tasks that are executed at the appropriate rates by its processing function. Tasks are scheduled in a rate-monotonic fashion—the periodic tasks with the highest rate of execution are executed first, followed by tasks in order of decreasing execution rate. This minimizes the variability in the period, particularly for the tasks with the highest execution rates. Task scheduling is static and fixed at compile time, so priority is deterministic.

States

Power-on Self-Test State

In the Power-On Self-Test (POST) state, the software exercises the user interface elements and executes a sequence of self-tests. At power-on, the beeper sounds a 250 ms, 2000 Hz tone. After the tone, the red LED flashes once for 500 ms. After the LED flash, the LCD flashes '88' once per second for the remainder of POST.

While the user interface elements are being exercised, the software executes a sequence of self-tests to confirm that the device hardware is operating correctly. In order to complete POST as quickly as possible, the tests run continuously until they complete, rather than utilizing a periodic task for execution. There are two periodic tasks in the POST state. A 250-ms task is used to produce the user interface sequences. A one-second task is used to service the watchdog.

Ready State

In the Ready state, the software looks for button input, flashes the green LED for a half second every two seconds and periodically runs self-tests according to schedule. There are three periodic tasks in the Ready state, executing with periods of 50 ms, 250 ms, and one second.

The 50-ms task is used to detect button presses, using the functions provided by the Button driver. The software looks for a dose request, defined as two button presses separated by at least 0.3 seconds and at most three seconds. The time is measured from the point of the first press to the point of the second release. On each detected button release, the software performs an Analog Switch Validation Test. When a dose request is detected, the software performs a Digital Switch Validation Test. If all tests pass, a transition to Dosing state is initiated.

The 250-ms task is used to produce the flashing sequence of the green LED. The green LED is turned on for half a second every two seconds.

The one-second task is used to schedule and execute self-tests, and service the watchdog.

Dosing State

The Dosing State is responsible for delivering the 170 µA drug delivery current over the 10 minute dose. For reference, 16 illustrates one variation of a the circuit controlling the anode and cathode. The current control block contains circuitry to connect the output of the voltage boost converter (VHV) to the anode electrode (EL_A) through the switch S1. The 10 bit DAC is used to configure the current output to a set value proportional to the desired dosing current. The DAC drives AMP1 which controls the current flowing through EL_A and EL_C by driving the gate of M2. The drain of M2 determines the current flow through Rsense which causes the voltage drop that is fed back into AMP1. As the skin resistance between EL_A and EL_C varies, so does the current through Rsense, which triggers a change in the output of AMP1. The VLOW signal is used in mode 0 to monitor the output of AMP1 as it approaches the saturation point of 2 volts. AMP1 becomes saturated if there is not sufficient voltage to deliver the programmed current with the resistance between EL_A and EL_C. Driver functions are available to control and monitor various the points of this circuit.

The Dosing State is grouped into three sub-flows: dose initiation sequence, dose control and dose completion sequence. Upon transition from Ready state to Dosing state the dose initiation sub-flow is started. In dose initiation the software configures the various points of the current control block and verifies their proper operation. The dose control sub-flow is then started. This flow controls the device over the 10 minute dose, monitoring for error conditions and controlling boost voltage to conserve power. Finally, the dose completion sub-flow is started. This flow disables drug delivery and verifies correct operation of the current source by measuring the various points in the current control block.

The dose termination sequence is always run on exit of the Dosing state independent of the event that caused the software to exit the Dosing state. The dose termination sequence always opens S1, sets the current source DAC to 0, sets the boost voltage to 0 and disables the boost circuit. Further, the dose termination sequence disables both the green LED and beeper. In some cases the dose termination sequence carries out actions already completed in the sub-flow processing. Almost all error cases in the Dosing State flow are handled similarly—with a resulting transition to dose termination. The exception to this is the handling of Poor Skin Contact detection.

If an error occurs during dose initiation or dose completion the software exits the Dosing State, completes the dose termination sequence and transitions to End of Life. Likewise, if an error other than Poor Skin Contact is encountered during dose control, the software completes the dose termination sequence and transitions to End of Life. When a Poor Skin Contact error is encountered in the Dosing State, the software immediately starts the dose completion sequence, but the dose count is not updated. When an error occurs in the dose completion sequence the software immediately completes the dose termination sequence and transitions to End of Life.

There are three periodic tasks in the Dosing state, executing with periods of 50 ms, 500 ms and one second.

The 50-ms task is used to detect dose requests while in the dosing state. The double button press detection mechanism is identical to Ready mode, except switch validation tests are not run. If the software detects a double button press in the dosing state, the dose request counter is incremented. This count is logged during dose-completion, but not when handling a Poor Skin Contact error.

The 500-ms task is used only the first time its tick occurs. On that first occurrence, the beeper is disabled.

The one-second task in this example is used to schedule the dose control sub-flow and service the watchdog. The one second task also schedules the slower rate Dosing State self-tests (i.e. the ADC and Reference Voltage test, Oscillator Accuracy Test, Battery Voltage Test and Software Timer Integrity Test).

Figure 17:
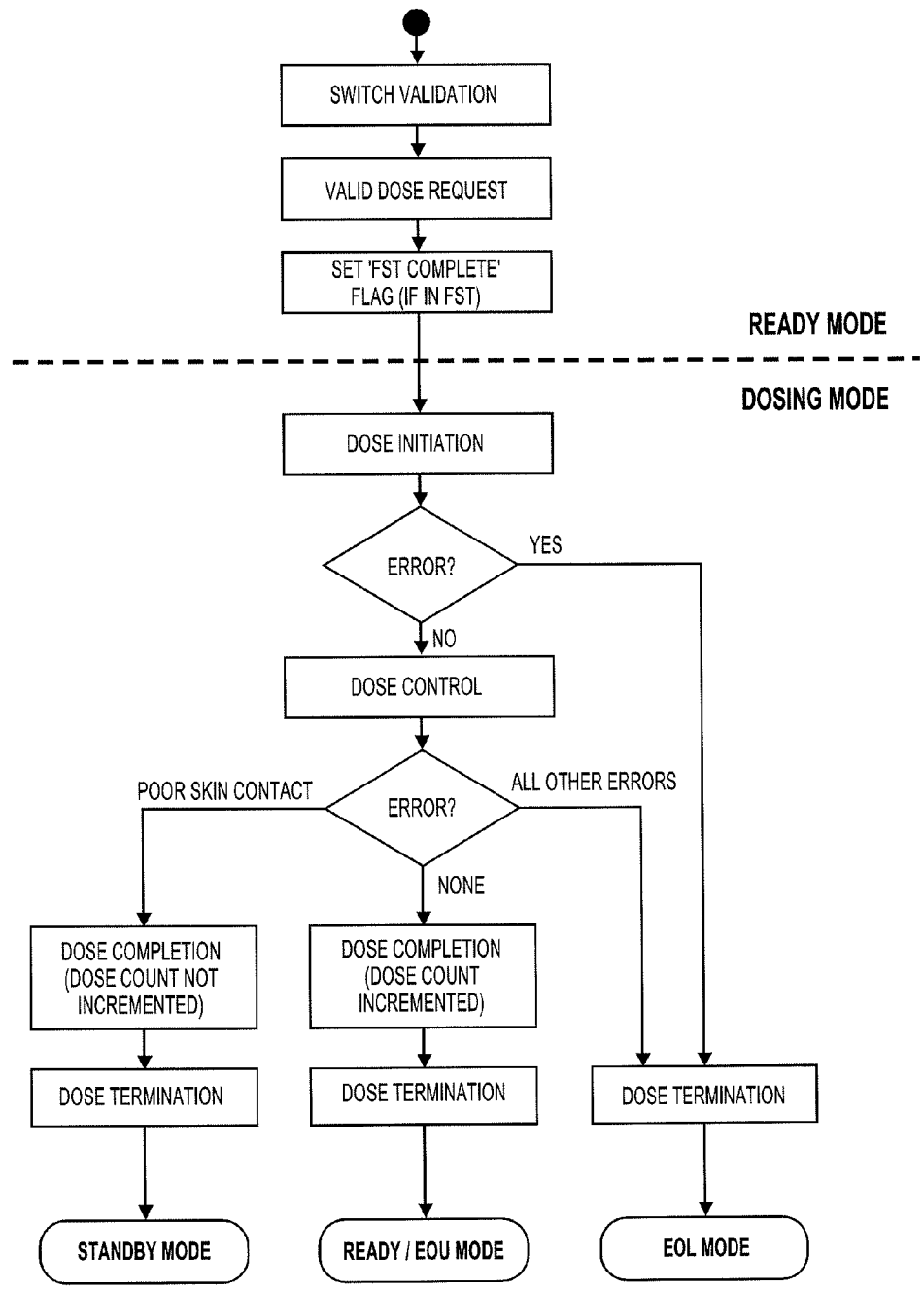
FIG. 17 shows a Dosing Mode Flow Diagram.

FIG. 17 shows a Dosing Mode Flow Diagram illustrating the high-level flow between each of the dosing mode sub-flows, the dose termination sequence and the transition to other states.

Dose Initiation Sequence

The dose initiation sequence starts by completing the sequence of turning on the green LED and enables the piezo beeper at 2000 Hz for a duration of 500 milliseconds. The software then completes the required self-tests for dosing mode entry. At this point the software begins to configure the device for drug delivery.

Figure 18:
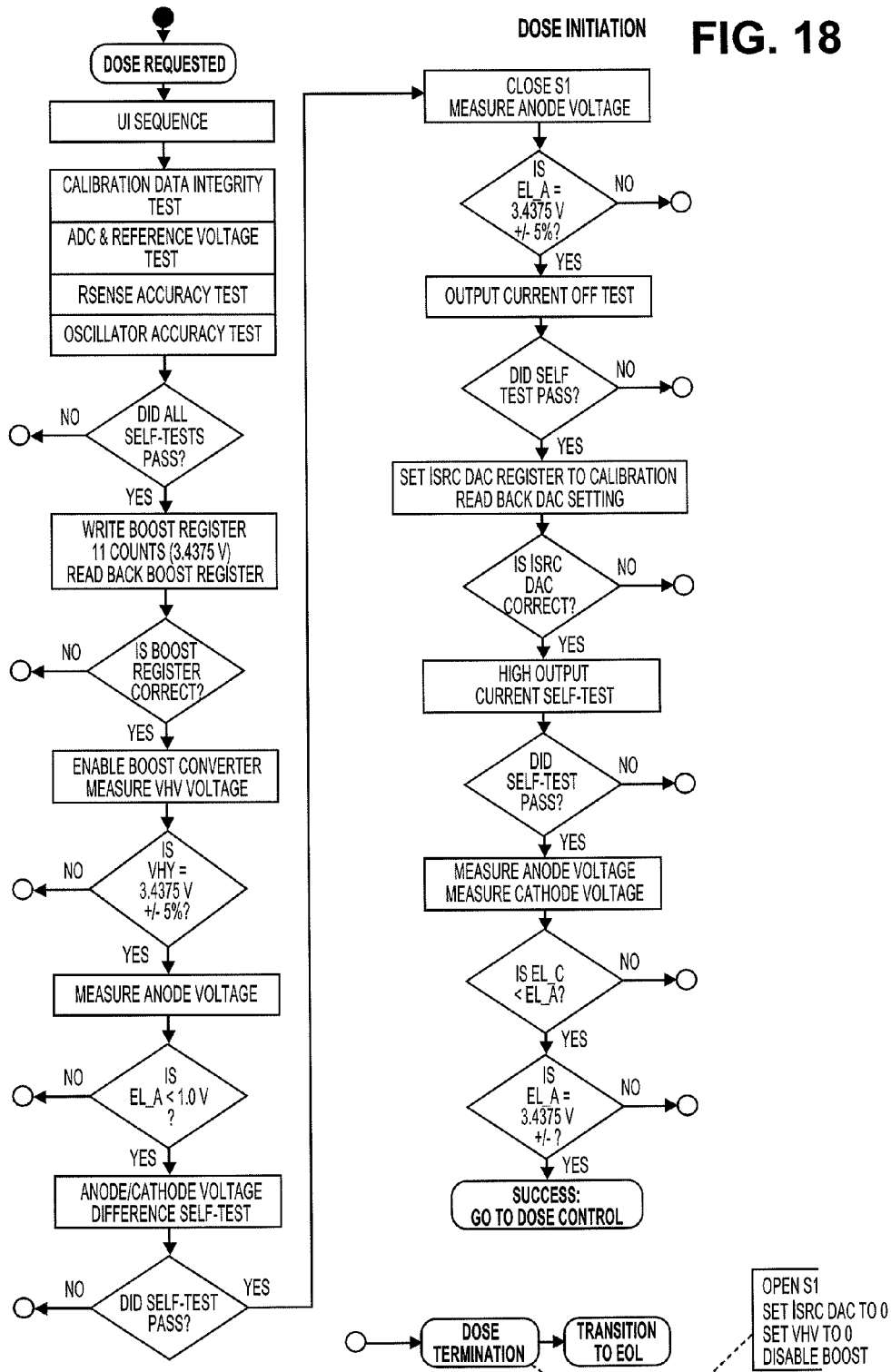
FIG. 18 shows a Dose Initiation Flow Diagram.

First the software writes the initial boot voltage setting of 3.4375 V and reads back the register to verify the write. Next, voltage boost is enabled and the software confirms that the boost circuit is operational by measuring the boost voltage using the ADC. The software then verifies that S1 is open by measuring the voltage on EL_A and confirming that it is below 1.0 V. The software verifies that there is not a large potential difference between the anode and cathode by completing the Anode/Cathode voltage difference test. Next, S1 is closed and the voltage on EL_A is measured again to confirm that S1 is closed. The software verifies that the output current is off by conducting the Output Current Off self-test. At this point the software sets the current source DAC to the calibrated value to start current flow. The software reads back the register to verify the write. The software next conducts the High Output Current self-test to verify that the current source is within range. Finally, the software measures both the anode and the cathode and conducts two checks. The first verifies that there is a voltage difference between EL_A and EL_C; the second verifies that the boost circuit is still able to supply the voltage with current enabled. If the measured values are not as expected, the software has detected an error, completes the dose termination sequence and transitions to End of Life. FIG. 18 shows a Dose Initiation Flow Diagram.

Dose Control Sequence

Upon successful completion of the dose initiation sequence the software enters dose control. The software starts the dose countdown timer with a duration of 10 minutes and begins the dose control loop on a 1 second period.

Each time through the loop the software first verifies that the output current is below 187 µA by completing the High Output Current self-test. Next, the software verifies that EL_A is within tolerance of the current VHV setting. After 1 minute has elapsed the Compromised Skin Barrier Test is performed each time through the loop and after 4 minutes has elapsed the Poor Skin Contact Test is performed each time through the loop.

After the self-tests are completed the software enters the VHV control portion of the loop. The software controls VHV to provide enough voltage to deliver the drug current while minimizing power consumption. The VHV control loop ramps the voltage to the necessary level, starting at 3.4375 V but never going above 11.25 V. To control VHV the software monitors the state of the VLOW signal. The VLOW signal is configured to monitor the gate voltage of M2. The signal is asserted when the output of AMP1 exceeds 2 V. The VLOW signal indicates that AMP1 is not able to deliver the 170 µA current because there is not sufficient source voltage. If the VLOW signal is asserted, the software increments VHV by 1 count (0.3125 V), up to a maximum of 11.25 V. The first several iterations through the control loop ramp VHV to the necessarily level, depending on the skin resistance. If skin resistance increases during the dose, the VLOW signal is asserted and VHV is incremented accordingly.

To conserve power and handle decreasing skin resistance during dose delivery, the software decrements VHV periodically. The decrement is triggered by a 20 second timeout. The timeout is set to 0 each time VHV is either incremented or decremented. The timeout is incremented each time that the control loop detects that the VLOW signal has not been asserted. When the timeout reaches 20 (i.e. 20 seconds) VHV is decremented. If the skin resistance has not changed the VLOW signal is asserted and the software increments VHV back to the necessary level the next time through the loop. Otherwise, VHV stays at the new voltage setting until the next timeout or the VLOW signal is asserted.

Finally the dose control sequence schedules the Dosing Mode self-tests that occur with periods greater than 1 second. These tests are the ADC and Reference Voltage test, Oscillator Accuracy Test, Battery Voltage Test and Software Timer Integrity Test. If any of these self-tests fail the software completes the dose termination sequence and transitions to EOL.

Figure 19:
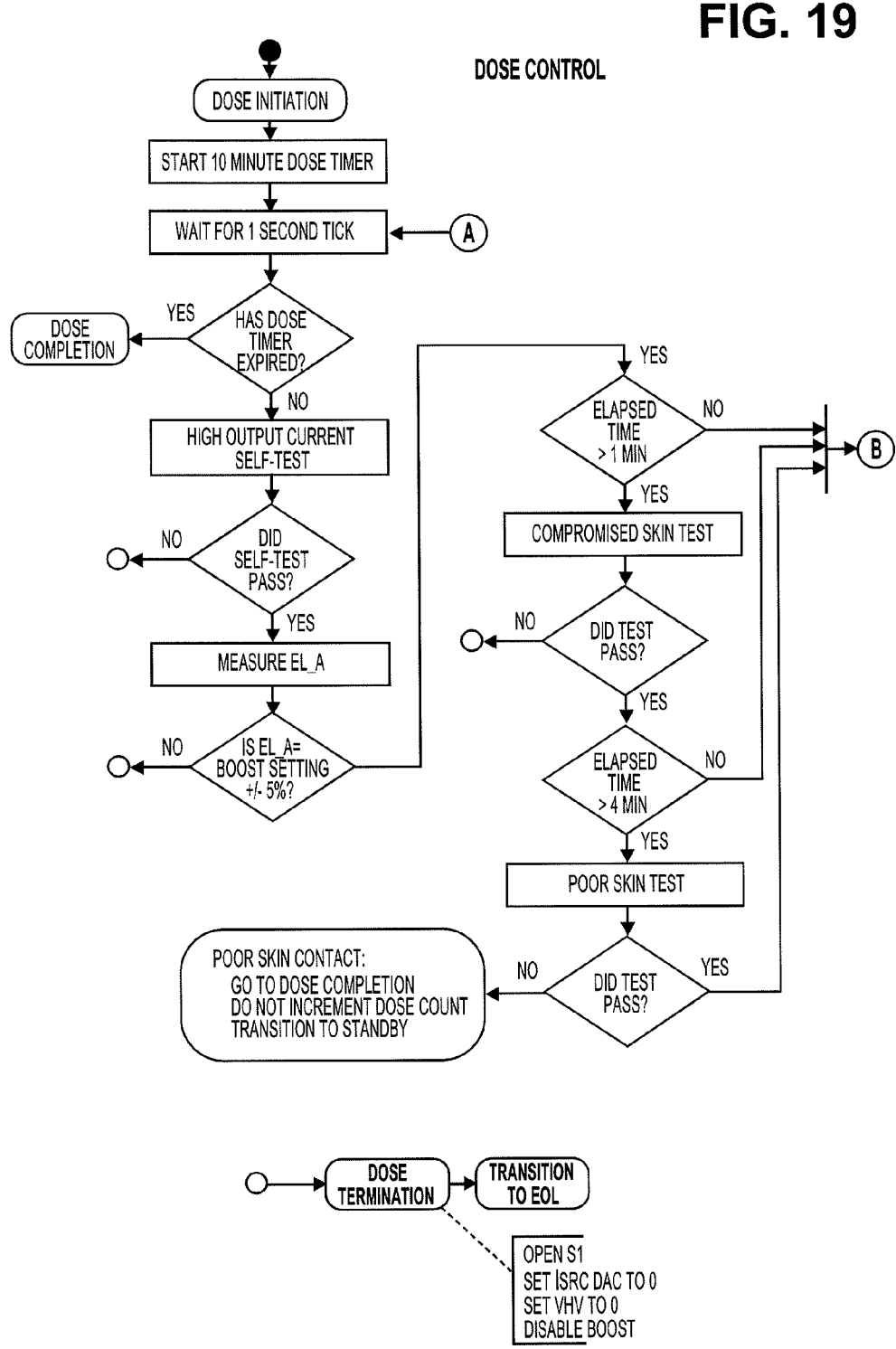
FIG. 19 shows a Dose Control Flow Diagram.
Figure 19:
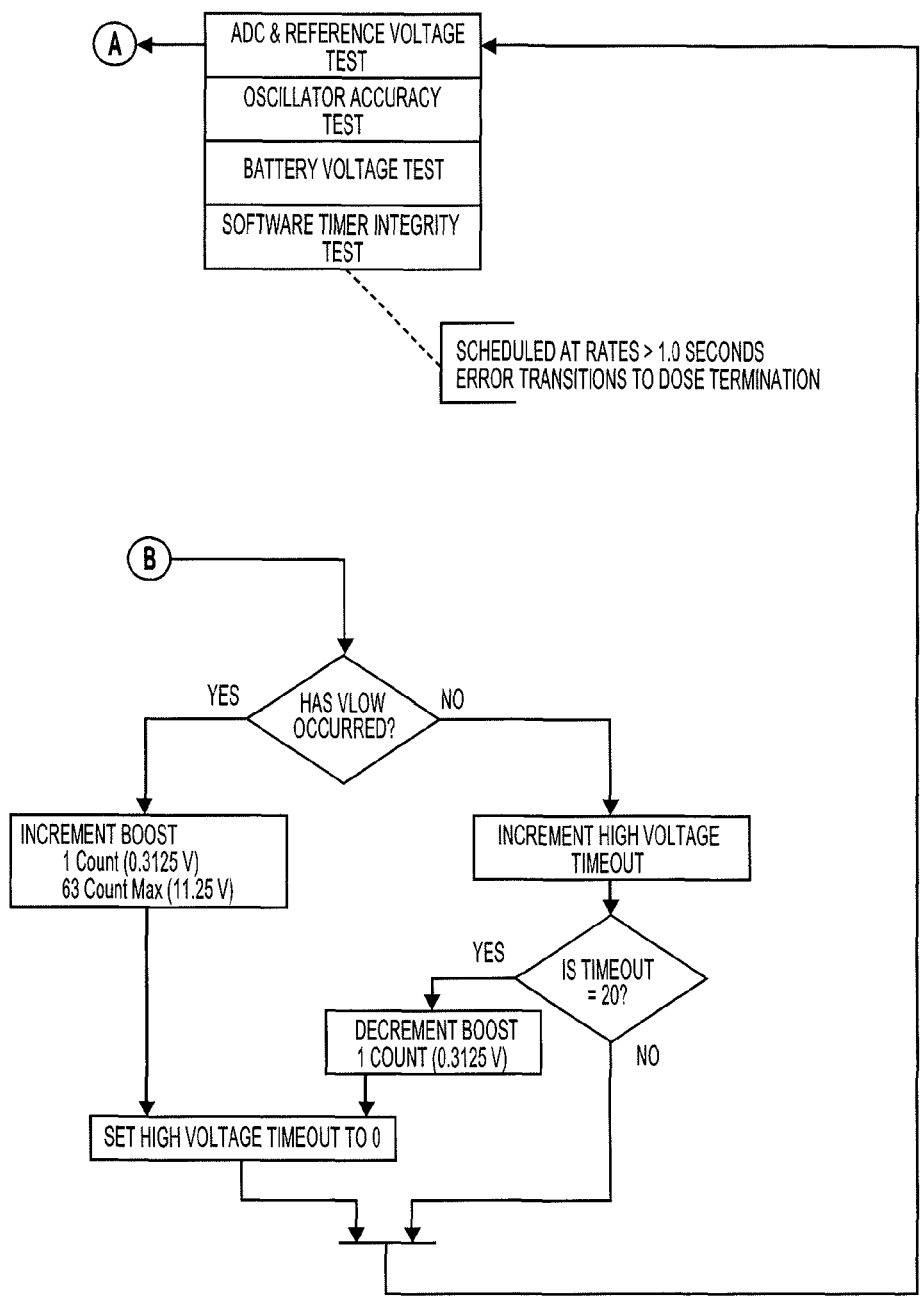

If an error other than Poor Skin Contact is encountered during the control loop, the software completes the dose termination sequence and transitions to End of Life. If Poor Skin Contact is detected, the software starts the dose completion sub-flow, but does not increment the dose count. The dose control loop is exited under normal conditions once the 10 minute dose time has elapsed. FIG. 19 shows the flow for dose control.

Dose Completion Sequence

The dose completion sequence is started on successful delivery of a dose or when a Poor Skin Contact is detected. First the software opens S1 and sets the current source DAC to 0 counts. The register write is read back and verified. Next the software conducts the Output Current Off self-test to verify that current is not above the leakage threshold. The software sets VHV to 0 V and verifies the register write by reading it back. The software verifies that VHV is off by measuring VHV and verifying that it less than 4.0 V; the expected value is Vbat. Next, the software disables the boost circuit and verifies the register write. The anode voltage is measured to verify that the potential is low. Next, the Anode/Cathode voltage difference test (the off-current test) is completed.

Figure 20:
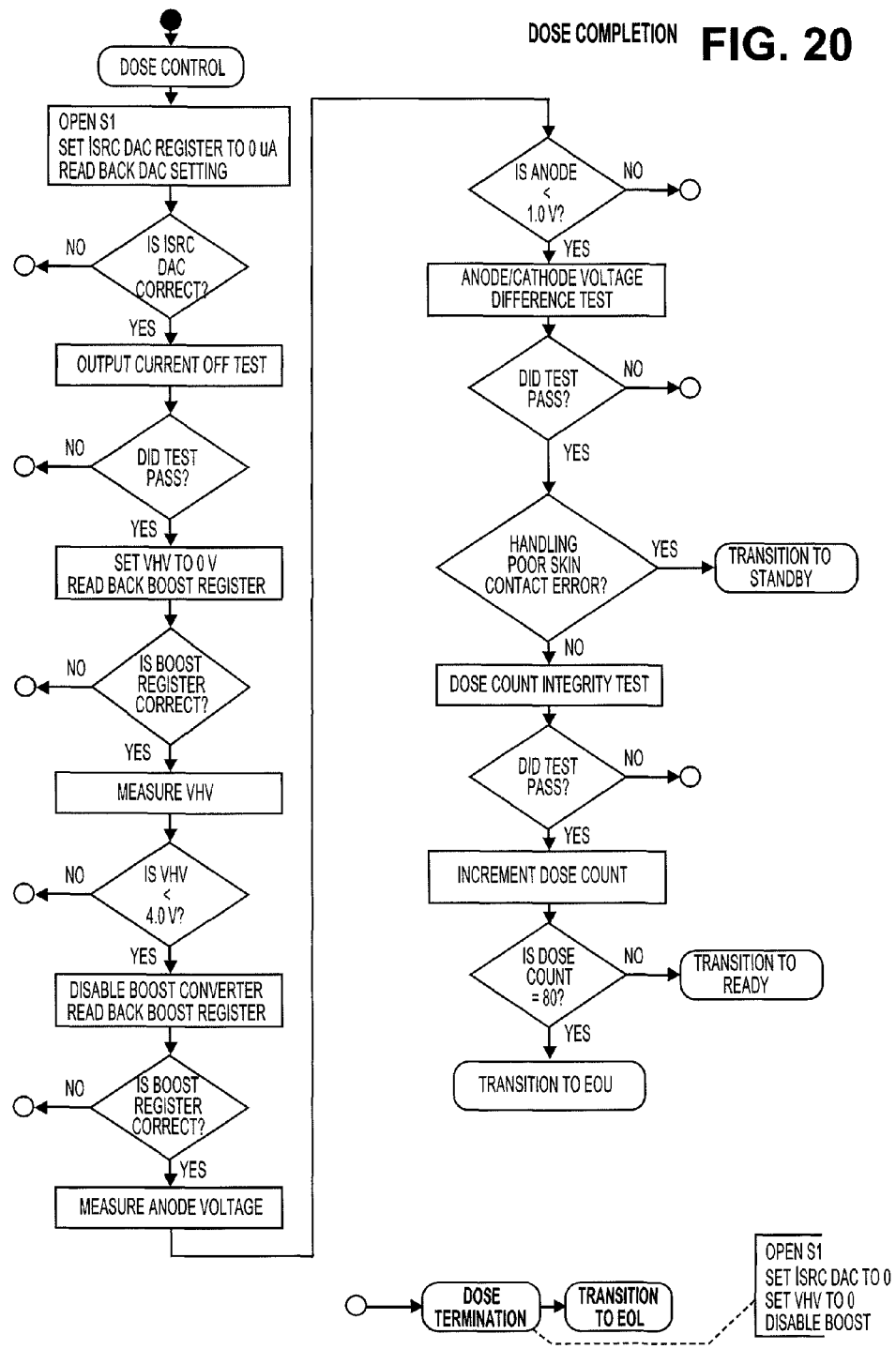
FIG. 20 shows a Dose Completion Flow Diagram.

If the software is handling Poor Skin Contact detection, it exits the dose completion sequence and transitions to Standby. Otherwise, the software performs the dose count integrity test, if the test passes the dose count is incremented and the LCD is updated. If the dose count is 80, the software transitions to End of Use, otherwise the software transitions to Ready. If the software detects an error in the dose completion sequence, the dose termination sequence is completed and the software transitions to End of Life. FIG. 20 shows one example of a flow diagram for dose completion.

Standby State

The Standby state is used to indicate that poor skin contacted was detected during the Dosing state. On entry to the state, the software logs a standby record with timestamp to NVM. While in Standby state, the output current is disabled, self-tests are suspended, and the software flashes the red LED twice a second and plays a sequence of long and short tones on the beeper. After 15 seconds, the software transitions to the Ready state.

The 250-ms task is used to produce the flashing sequence of the red LED and the tones played on the beeper. This task is also used to detect when 15 seconds have passed and initiates the transition to the next state.

The one-second task is used to service the watchdog.

End of Use State

The software enters the End of Use state when the device has reached its 80 dose limit or its time limit of 24 hours. On entry to the state, the software logs the finish code, timestamp, and battery voltage to NVM. While in End of Use state, the output current is disabled, the final dose count is displayed on the LCD, and the red LED flashes. The software monitors the button for a press and hold event, and periodically executes self-tests.

The 50-ms task is used to detect button presses, using the functions provided by the Button driver. If the software detects a button press and hold for 6 seconds, a transition to Shutdown state is initiated.

The 250-ms task is used to produce the flashing sequence of the red LED.

The one-second task is used to schedule and execute self-tests, and service the watchdog. This task is also used to run the Battery Voltage Test once every 10 minutes. If the battery is below the low voltage threshold, the software initiates a transition to the End of Life State.

End of Life State

On entry to the End of Life state, the software logs the reason for transition, the timestamp, and the battery voltage to NVM. The device may enter the End of Life (EOL) state when forced by errors (including failing a self-test such as the off-current test). While in End of Life state, the output current is disabled, the red LED flashes and the beeper sounds a sequence of short tones. The software monitors the button for a press and hold event, and periodically checks the battery level every 10 minutes.

The 50-ms task is used to detect button presses, using the functions provided by the Button driver. If the software detects a button press and hold for 6 seconds, a transition to Shutdown state is initiated.

The 250-ms task is used to produce the flashing sequence of the red LED and produce the short tones on the beeper.

The one-second task is used to schedule and execute self-tests, and service the watchdog. This task is also used to run the Battery Voltage Test once every 10 minutes. If the battery is below the depleted threshold, the software initiates a transition to the Shutdown State.

Shutdown State

The Shutdown state is the final state of the device. On entry to the state, the software logs the reason for transition, the timestamp, and the battery voltage to NVM and disables the LEDs, the LCD, and the beeper.

While in the Shutdown state, the output current is disabled. The software does nothing but service the watchdog using the one-second task. The software does not exit this state.

Self-Tests

As discussed above, the system or device may include a set of self-tests to monitor the device operating parameters to detect faults in device hardware or software, or in usage conditions. The off-current module may be one form of a self-test. The self-test may derive from requirements, risk and reliability analysis activities. The tolerance ranges specified for test limits derive included herein (including the thresholds such as the Off-Current Threshold) are exemplary only. These example tolerances may depend upon tolerances of hardware components. Software, hardware and firmware (including logic/algorithms) of the self-tests may check against a specific limit value that does not vary.

Self-Test Scheduling and Sequencing

The subset of self-tests run and the scheduling of those tests may vary depending on the device's operating mode, as discussed above. FIG. 21 shows table 1, which shows self-tests that can be run in each mode and when those tests run. Standby Mode is not shown because self-tests are deferred until the return to Ready Mode. Standby lasts only 15 seconds, and with the most frequent tests running only once a minute in non-dosing modes, Standby mode would be exited before any tests would run.

The test scheduling indicated in FIG. 21 is in some cases more frequent than would be suggested by the detection times stated in the requirements. This allows for an implementation that requires several consecutive failures before a fault is set in cases where there may be significant variability of measured results from test to test. In the case of the Oscillator Accuracy Test, this allows fault detection within the required real time stated in the requirements, even if the oscillator is operating at the extreme low limit, just above the point of a hardware reset.

In many cases the correct execution of a particular test depends on the correct operation of other hardware, firmware and/or software elements that are checked by other tests. This may help determine an order in which tests must run for valid results. Predecessor tests are those that must pass before the result of a given test can be considered valid. For example, the ADC and Reference Voltage Test must pass before any test using the ADC runs.

One special case is the ROM Test. Because all code, including that for the ROM Test, is stored in ROM, it's not possible to pass the ROM Test prior to using ROM.

RAM Test

The RAM Test verifies that each address in RAM can be read and written to. The test is performed in assembly language startup code, before RAM and stack initialization or C startup. The values 0x55 and 0xAA are written to and then read from each byte of RAM to verify every bit is functioning. The test first writes 0x55 to each byte of RAM. Then it reads each byte, compares it to 0x55, and writes 0xAA to the byte. Finally, it reads each byte of RAM and compares the values to 0xAA. If any of the comparisons fail, the test fails. Otherwise, the test passes.

ROM Test

The ROM Test verifies the contents of ROM. The test calculates an 8-bit checksum of ROM, which is a summation of all the values in ROM. At manufacture the last byte of ROM will be set so that the checksum will equal 0xFF. When the test is run, it calculates the checksum for the ROM and compares it to 0xFF. If the checksum is not equal to 0xFF, the test fails. Otherwise, the test passes.

Calibration Data Integrity Test

The Calibration Data Integrity Test verifies the contents of calibration data stored in the internal EEPROM. These data include the boot flag, the oscillator limit values, the calibrated current source DAC setting, the Rsense reading when pulled-up, and trimming values for the ADC and oscillator. These values are encoded with error detection and correction codes. The first time the calibration data integrity check runs, it decodes all calibration values via the EEPROM driver and fails if the EEPROM driver detects uncorrectable data corruption in any of the values.

After being validated by a successful first integrity test, the ADC calibration values are stored in RAM to improve the performance of the ADC driver. On subsequent integrity checks of these values, the test compares the values stored in RAM with the values stored in EEPROM. This reduces processing time by avoiding the overhead of decoding error codes. The test passes if the values in RAM and EEPROM match and fails otherwise.

For all calibration data other than the ADC calibration, subsequent integrity tests behave the same as the first. Error codes are decoded for all values, and any uncorrectable corruption results in a test failure.

Oscillator Accuracy Test

The Oscillator Accuracy Test verifies the accuracy of the oscillator frequency using the frequency-to-voltage conversion channel of the ADC. During manufacturing, the oscillator is calibrated to 2.048 MHz±1%, and frequency-to-voltage readings at high and low limits are stored in non-volatile memory. The stored limits are between +3% and +5% on the high side, and −3% and −5% on the low side.

The tolerance on the frequency-to-voltage converter is ±5%. The stack-up of these tolerances may result in the detection threshold being close to but not more than 10% from nominal, which is within the required ±10% limits of the Oscillator Accuracy Test.

When the Oscillator Accuracy Test runs, the 12-bit ADC frequency-to-voltage reading is compared to the two 12-bit limit values stored in non-volatile memory. If the ADC reading is not within limits, the test fails. Otherwise, the test passes.

In order to detect an oscillator error within in the required real time in the case where the oscillator is running slow, the test will run more frequently than it would if the oscillator were running at a nominal frequency. reset occurs at 0.8 MHz. This is a divider of 2.5 on the nominal value of 2.048 MHz, and the same divider must be applied to the test scheduling period. For example, in order to assure detection of a low-limit oscillator within 10 minutes, the test must run every 4 minutes.

ADC and Reference Voltage Test

The ADC and Reference Voltage Test verifies the correct operation of the ADC, the ADC multiplexer, and the relative levels of the ADC reference voltage and the Main reference voltage. The test measures the Main reference voltage using the ADC and compares it to 1 volt. In order for the test to pass, the ADC, the ADC multiplexer, the Main voltage reference and the ADC voltage reference must all be functioning correctly. If the test fails, the component that is failing cannot be determined. The test fails if the Main reference voltage is greater than 1.1 volts or less than 0.9 volts. Otherwise the test passes.

Software Timer Integrity Test

The Software Timer Integrity Test verifies the rate of the primary software timers using a secondary software timer. The secondary software timer is given a countdown length and the current value of one of the primary timers. During Ready mode, the secondary timer initiates a check of the primary system time every ten minutes. During Dosing mode, the secondary timer initiates a check of the primary doing timer every minute. After counting down for the specified length of time, the secondary timer compares the current primary timer value to the initial value. If the values differ by more than 10% the test fails. Otherwise, the test passes.

Dose Count Integrity Test

The dose count integrity test verifies that the dose count value in RAM has not become corrupted. A redundant copy of dose count is stored in the internal EEPROM and initialized to zero. The test is run on successful dose competition. Before incrementing the dose count, the current value stored in RAM is compared against the copy in EEPROM. If the two values match, they are both incremented and the EEPROM value is committed. If the two values do not match the test fails.

Rsense Accuracy Test

The Rsense Accuracy Test verifies the accuracy of the Rsense resistance value. The Rsense resistor has a tolerance of 1%. During manufacturing, the Rsense pull-up is enabled and the voltage at Rsense is measured with the ADC. The 12-bit ADC value is written to the RSENSE location in NVM. This test duplicates that manufacture measurement. The Rsense pull-up is enabled and the ADC is used to measure the Rsense voltage. The measurement is compared to the one stored in NVM. The test fails if the two values differ by more than 5%. Otherwise, the test passes.

Battery Voltage Test

The Battery Voltage Test returns the state of the battery relative to several threshold values. The test measures the battery voltage using the ADC and compares it to the battery thresholds. The test reports the battery is good if the voltage measurement is greater than 2.7 volts +/−5%. The test reports the battery is low if the voltage measurement is less than 2.7 volts +/−5% and greater than 2.3 volts +/−5%. The test reports the battery is depleted if the voltage measurement is less than 2.3 volts +/−5%.

Analog Switch Validation Test

The Analog Switch Validation Test measures the voltage levels on both the high and low sides of the dose button switch in order to detect potential problems that could lead to erroneous switch readings. Under normal conditions with the switch open, voltage on the high side of the switch will be slightly less than battery voltage after accounting for the small voltage drop caused by the electronic components connected to the switch circuit. Under normal conditions, the voltage on the low side of the switch will be very close to ground.

Some conditions, such as contamination or corrosion, can cause the high-side voltage to drop or the low-side voltage to rise. If the high-side voltage falls to less than (0.8×battery voltage), or the low-side voltage rises to greater than (0.2× battery voltage), the switch input is in a range of indeterminate digital logic level with respect to the digital switch input. A switch voltage in this range could result in erroneous switch readings, which could manifest as false button transitions that were not initiated by the user. The Analog Switch Validation Test detects the condition before the switch voltage levels reach the point where erroneous readings could occur.

The Analog Switch Validation Test must run when the switch is in its normally-open condition so that the high- and low-side voltages can both be measured. Any change in the switch state while the test is running could cause the test to falsely fail due to measurement of the high-side voltage while the switch is closed. The user may press or release the button at any time, but there are mechanical and human limits on the minimum time between presses. Therefore, the point where the switch state is known to be open with the greatest certainty is immediately following a detected release of the button.

The Analog Switch Validation Test runs immediately following each detected button release. It uses the ITSIC ADC to make sequential measurements of the high-side voltage, the low-side voltage, and the battery voltage. The ADC is configured to sample for 6.25 ms for each measurement. If the voltage on the high side of the switch is less than or equal to (0.8×battery voltage), or if the voltage on the low side is greater than or equal to (0.2×battery voltage), the test fails.

Digital Switch Validation Test

The Digital Switch Validation Test is similar in purpose to the Analog Switch Validation Test, but it may be simpler, faster, and coarser in its measurements.

The test uses secondary digital inputs, connected to each side of the dose button switch, to confirm the digital logic levels while the switch is open (button not depressed). The secondary digital inputs are of the same type as the primary digital inputs, and the corresponding values are expected to match.

The Digital Switch Validation Test runs after the Analog Switch Validation Test of the second button release of a double-press that meets the criteria for a dose initiation sequence. If the secondary digital input on the high side of the switch is low, or if the secondary digital input on the low side of the switch is high, the test fails.

Output Current Off Test

In some variations, the off-current module may be configured to perform an Output Current Off Test. The Output Current Off Test may verify that the leakage current is less than some threshold (e.g., 3 μA, 9 μA, etc.) when the current source is off. The test may calculate the leakage current from the measured Rsense voltage and the low-limit Rsense resistance of 3.96 kOhms.

$$I_{leakage} = \frac{V_{Rsense}}{R_{Rsense}}$$

$$V_{Rsense} = I_{leakage} * R_{Rsense}$$

$$V_{Rsense} < (3 \ \mu A * 3.96 \ kOhms)$$

$$V_{Rsense} < 12 \ mV$$

The test measures the Rsense voltage using the ADC while the current source is off. Thus, in some variations, if the Rsense voltage measurement is greater than some threshold (e.g., 12 mV, 36 mV, etc.) the test fails. Otherwise, the test passes.

Anode/Cathode Voltage Difference Test

In some variations the off-current module may also be configured to perform an Anode/Cathode Voltage Difference Test. The Anode/Cathode Voltage Difference Test may verify that when S1 is open and the current source is disabled, there is little voltage difference between the anode and the cathode. This test may check for the failure case of current flow from anode to cathode resulting from any fault in the output circuit. The test measures the anode voltage and the cathode voltage using the ADC and calculates the voltage difference between the two points. The test fails if the voltage difference is greater than some threshold (e.g., 0.85 V, 2.5 V, etc.). Otherwise, the test passes.

High Output Current Test

The High Output Current Test verifies that the dosing current is less than 187 μA. The test measures the voltage at Rsense using the ADC and uses that voltage to calculate the current.

$$I_{dosing} = \frac{V_{Rsense}}{R_{Rsense}}$$

$$V_{Rsense} = I_{dosing} * R_{Rsense}$$

$$R_{Rsense} < (187 \ \mu A * 3.96 \ kOhms)$$

$$V_{Rsense} < 741 \ mV$$

An Rsense resistance at the low limit of 3.96 kOhms will result in the lowest measured Rsense voltage at 187 μA. The test fails if the measured Rsense voltage is greater than 741 mV. Otherwise, the test passes.

Poor Skin Contact Test

The Poor Skin-Contact Test verifies that the skin resistance is less than 432 kOhms +/−5%. The test measures the voltage at Rsense using the ADC and uses that voltage to calculate the skin resistance.

$$I_{dosing} = \frac{V_{Anode} - V_{Cathode}}{R_{Skin}}$$

-continued $$I_{dosing} = \frac{9.25 \ V}{432 \ kOhms} = 21.4 \ \mu A$$

$$V_{Rsense} = I_{dosing} * R_{Rsense}$$

$$V_{Rsense} > 21.4 \ \mu A * 3.96 \ kOhms$$

$$V_{Rsense} > 84.7 \ mV$$

At 432 kOhms, this example assumes that the difference between the anode and the cathode is 9.25 V. Since the Rsense has a tolerance of 1%, 3.96 kOhms is the lowest resistance it could have. The test fails if the voltage at Rsense is less than 84.7 mV. Otherwise, the test passes.

Compromised Skin Barrier Test

The Compromised Skin Barrier Test verifies that the skin resistance is greater than 5000 Ohms +/−5%. The test measures the cathode voltage and the anode voltage using the ADC. The test uses these two measurements to calculate the skin resistance.

$$R_{Skin} = \frac{V_{Anode} - V_{Cathode}}{I_{dosing}}$$

$$V_{Anode} - V_{Cathode} = I_{dosing} * R_{Skin}$$

$$(V_{Anode} - V_{Cathode}) > (170 \ \mu A * 5000 \ Ohms)$$

$$(V_{Anode} - V_{Cathode}) > 0.85 \ V$$

The test fails if the difference between the anode voltage and the cathode voltage is less than 0.85 V. Otherwise, the test passes.

Drivers

The low-level hardware drivers provide functions to configure and use the corresponding system hardware. The drivers do not maintain timing information. Modules that use the drivers must manage any necessary timing. In some cases the drivers maintain state information pertaining to the hardware to which they provide an interface.

Timer

The Timer driver uses the hardware timers in the CPU to provide a variety of timing functions, including: (a) a system tick driven by a periodic interrupt every 8 ms; (b) periodic ticks derived from the system tick and occurring every 50, 100, 250, 500, or 1000 ms; (c) a system timer that counts the number of seconds since power was applied to the system; (d) a dose timer that counts down the duration of a dose, in seconds; and (e) a button timer that counts down the time window for a button double-press for dose initiation.

The Timer driver uses hardware Timer0 as an 8-bit timer in auto-reload mode to provide the 8-ms system tick. Timer0 generates an interrupt each time it rolls over. To minimize interrupt processing time, the interrupt handler simply increments an 8-bit counter, sets a local flag indicating that the system tick occurred, and samples the button input (see Section 5.4.2 Dose Button). The driver provides a function for the main loop to check for occurrence of the tick. The 8-bit counter rolls over every 2.048 seconds. This allows generation of periodic ticks with periods up to that value.

When the main loop sees that the system tick has occurred, it calls the timer processing function, which updates software timers as appropriate. This function uses the system tick counter to decrement the dose and/or button timers once per second if they are active, and increment the system lifetime timer once per second. It also clears the system tick flag, indicating that processing is complete for that tick.

The Timer driver uses the system tick to calculate periodic ticks with periods that are multiples of the system tick. Nominally the periods available are 50, 100, 250, 500, or 1000 ms. However, not all these periods are integer multiples of 8 ms, so the exact period is less in some cases, due to truncation. The Timer driver provides functions to check for the occurrence of each periodic tick, as well as a function to synchronize all periodic ticks to the current system tick value.

Dose Button

The Dose Button driver contains functions for sampling, debouncing, and detecting transitions on the button input.

The button input is sampled every 8 ms in the Timer driver periodic interrupt handler. This is necessary to achieve button sampling at a regular and sufficiently high rate. Execution of each iteration of the main loop spans several periodic interrupts and varies in duration with execution path.

The button is sampled into a circular buffer that holds eight samples. The six most recent samples are used by the debounce algorithm to determine the state of the button. All six samples must be the same to identify a valid button state. If the buffer contains a mix of low and high sample values, the button is determined to be in a bouncing or transition state. The Button driver keeps track of the state of the button from the previous time the debounce algorithm was applied and can thus identify transitions. A function is provided to check for a button release. It can be called approximately every 50 ms by tasks reading the button to provide acceptable user responsiveness to inputs. A release transition requires at least six samples with the button depressed, followed by at least six samples with it released. Therefore approximately 100 ms of sampling is required to identify a button press.

LCD

The LCD driver provides the software interface for displaying a two-digit number on the LCD. The driver supports display of integers 0-99. Input values 0-9 do not display a leading zero. The driver also exposes the LCD control functions: enable, disable, and blank The left and right digits are designated Digit 1 and Digit 2 respectively. Each of the two digits has seven segments. Segments are labeled A-F, starting with the top segment and moving clockwise; the center segment is labeled G. The ITSIC may be capable of driving up to 80 LCD segments. There are 20 segment control lines and 4 backplane lines (also called common lines) that are multiplexed to control each of the available 80 segments. In this application only 14 LCD segments are used with all 4 backplanes.

LED

The LED driver provides the software interface for controlling green and red LEDs. Fixed current settings are used to drive the LEDs according to the device's power budget. The green LED is connected to the LED1 current source and driven at 2.5 mA. The red LED is connected to the LED2 current source and driven at 1.4 mA. The driver uses the LED_BEEP register to turn on, turn off or toggle each LED.

Beeper

The Beeper driver provides the software interface for controlling the audio transducer. The operating frequency range is 1000-4875 Hz in 125 Hz steps.

When turning on the audio transducer, the driver configures the transducer to be driven by the voltage boost circuit. This allows for control of the audio volume by adjustment of the boost voltage. However, the driver does not set voltage boost. The application is responsible for setting the appropriate boost level before enabling the transducer. Voltage boost can be configured using the Boost Controller driver.

The driver controls the audio transducer through the LED_BEEP and BEEP_FC registers.

Voltage Boost Controller

The Voltage Boost Controller driver provides the software interface for controlling the voltage boost block. This circuit is responsible for boosting battery voltage to the higher levels required to maintain dosing current output or drive the piezo audio transducer at sufficient volume.

The driver supports boost levels over the full operating range: 0.0 to 19.6875 volts in 0.3125 volt steps. The minimum boost voltage is determined by the battery voltage; settings below battery voltage result in output equal to battery voltage. The boost circuit charge time is configurable in hardware but set to a fixed value of 1.5 microseconds on driver initialization. Further, the driver provides functions for reading back the voltage control setting and enabling/disabling the boost circuit.

The driver provides a function to poll the boost over-voltage signal. The over-voltage signal is asserted if the voltage output exceeds 21.0 volts. The driver controls the boost circuit through the BOOST_0, BOOST_1, EOV and IT1 registers.

Current Controller

The Current Controller driver provides the software interface for controlling the current source block. The current source output level is controlled by a 10-bit DAC. The driver allows for current output over the full operating range of the current source. The driver controls the current source through the ISRC_0, ISRC_1, EVL and IT0 registers.

The driver provides functions to enable or disable the current source, set the DAC value, read back the DAC value, and enable or disable the Rsense pull-up resistor.

The driver also provides an interface to the current control block's low voltage signal (VLOW). During initialization this signal is configured to monitor the gate voltage of M2. A function to monitor the state of the signal is provided.

Trimming

The current controller requires trimming to achieve the desired accuracy at 170 µA. The uncalibrated current controller has an accuracy of ±5%, while the calibrated current controller has an accuracy of ±0.5%. The 10-bit DAC value to produce a current of 170 µA is determined and written to the ISRC_170 location in NVM during manufacture. This value is read from NVM and written to the ISRC registers when the current source is enabled.

Analog to Digital Converter (ADC)

The ADC driver provides the software interface for configuring and using the ADC. The ADC has 12-bit resolution with three possible input ranges, configurable conversion time, and selectable inputs. The ADC inputs are grouped by full-scale range: low (0.0 to 2.0 volts), medium (0.0 to 3.6 volts) and high (0.0 to 24.0 volts).

The driver provides a function for configuring the input select, specifying the conversion time and starting a conversion. The conversion time range is 0.78125 to 100 ms. The start-conversion function is non-blocking and the conversion is asynchronous. Completion of the conversion is signaled by the ADC done interrupt. The driver is responsible for handling this interrupt and storing the counts. A function is provided for the application to determine if an ADC read is in progress.

The ADC driver is responsible for applying calibration gain and offsets for the appropriate input range. The calibrations are applied when the application reads the result of a completed conversion. Calibrations are stored locally to the driver and a function is provided to return a reference to the data structure. This reference is used to populate the calibration values from NVM and to conduct the Calibration Data Integrity Test.

The driver controls the ADC through the ADC_CTRL, ADC_MSB, ADC_LSB and EADC registers.

Trimming

The output of the ADC must be trimmed to achieve the desired accuracy. The output of the ADC has a gain error of ±5% and an offset error of ±5%. After trimming, the ADC output has an accuracy of ±0.5%. The trimming calculation requires two 9-bit signed values from NVM for each of the three ADC ranges. Each gain and offset is stored as an 8-bit unsigned value in NVM and there is a 6-bit value that holds all the signed bits. Therefore, there are 7 values are written to NVM by the manufacture: ADC_GAIN_HIGH, ADC_OFFSET_HIGH, ADC_GAIN_MID, ADC_OFFSET_MID, ADC_GAIN_LOW, ADC_OFFSET_LOW, and ADC_SIGNS.

High Range $$ADC\_result = ADC\_out * \left(1 + \frac{ADC\_GAIN\_HIGH}{4096}\right) + ADC\_OFFSET\_HIGH$$

$$ADC\_result = (ADC\_MSB << 4) | (ADC\_LSB >> 4);$$

$$ADC\_result += ((ADC\_GAIN\_HIGH * ADC\_MSB) >> 8) \& 0 \times FF;$$

$$ADC\_result += ADC\_OFFSET\_HIGH;$$

Medium Range $$ADC\_result = ADC\_out * \left(1 + \frac{ADC\_GAIN\_MID}{4096}\right) + ADC\_OFFSET\_MID$$

$$ADC\_result = (ADC\_MSB << 4) | (ADC\_LSB >> 4);$$

$$ADC\_result += ((ADC\_GAIN\_MID * ADC\_MSB) >> 8) \& 0 \times FF;$$

$$ADC\_result += ADC\_OFFSET\_MID;$$

Low Range $$ADC\_result = ADC\_out * \left(1 + \frac{ADC\_GAIN\_LOW}{4096}\right) + ADC\_OFFSET\_LOW$$

$$ADC\_result = (ADC\_MSB << 4) | (ADC\_LSB >> 4);$$

$$ADC\_result += ((ADC\_GAIN\_LOW * ADC\_MSB) >> 8) \& 0 \times FF;$$

$$ADC\_result += ADC\_OFFSET\_LOW;$$

Watchdog

The Watchdog driver provides the software interface for initializing and servicing the watchdog. The watchdog timeout is configured to 6.144 seconds by the initialization function. If the watchdog is not serviced within this period, the watchdog hardware resets the processor. The watchdog timer is started on driver initialization. The application is responsible for servicing the watchdog.

ITSIC Core

The ITSIC Core driver provides the software interface for controller general functions related to the ITSIC. These functions include: enabling and disabling all interrupts via the general enable bit, and reading and writing the oscillator calibration value. The driver uses the EA and OSC_CAL registers. Upon initializing the driver the oscillator calibration is set to 0.0% with interrupts disabled.

Oscillator Calibration

The oscillator requires calibration to achieve ±1% accuracy in the 2.048 MHz system clock. The uncalibrated oscillator has an accuracy of ±30%. The 8-bit calibration value adjusts the frequency of the oscillator and is determined and written to the OSC_CAL_VALUE location in NVM during manufacture. The OSC_CAL_VALUE is read from NVM and written directly to the OSC_CAL register. After writing to the register, the oscillator requires a settling time of 1 mS.

Internal EEPROM

The ITSIC non-volatile memory is used by firmware for two purposes: persistent data storage and redundant storage of critical run-time data. The persistent storage includes device trimming data and the usage log. The redundant storage includes run-time data that has been identified as critical to safety through risk analysis. The firmware is designed to read from and write from non-volatile memory.

The ITSIC non-volatile memory is an 8 k on-chip EEPROM organized as a 128×64 bit array. EEPROM access is always an entire page (64 bits wide). The EEPROM is memory mapped and referenced from code via external data addressing. External data addresses are declared in code using the C51 xdata keyword.

To improve reliability thus lowering the effective error rate, the firmware applies error detection and correction mechanisms over the EEPROM. Three mechanisms are used, each with different integrity properties. Hamming codes are used to encode entire pages. Hamming codes are used to encode specific data fields when entire page coding is not needed. Finally parity bits are used to check integrity over data that are not used by the device during operation. The two Hamming codes are capable of correcting all 1-bit errors and detecting all 2-bit errors. Parity bits are capable of detecting any odd number of bit errors.

The software interface to the EEPROM may influence the design of the system, particularly data locality. Read access is transparent to the firmware. The core reads the entire page into a 64 bit shadow register. If the requested page is already loaded, the EEPROM is not read at all. Write access requires the firmware to control the page commit timing. A write access first reads the corresponding EEPROM page into the shadow register. When the firmware is ready to commit the page, it asserts a page clear for 1 ms, a page write for 1 ms and then resets both the page write and clear bits.

Driver Structure

The EEPROM driver encapsulates access to the EEPROM by providing functions to read from and write to the EEPROM. The driver provides functions to decode and read data from the EEPROM. These functions provide access to the device's calibration values, boot parameters and the device ID field.

The driver also provides function to validate the integrity of these values after device initialization. The validation functions compare the value stored in RAM with the value stored in EEPROM to ensure that the copy in RAM has not become corrupted.

Finally, the driver provides functions write to the EEPROM. These functions include usage logging and updating the device power-on-code. As needed the driver may handle Hamming encode and decode operations as well as calculating parity bits on write-only fields.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An electrotransport drug delivery device that prevents unwanted delivery of drug while in an off state when the device is powered on, the device comprising:
   an anode and a cathode;
   an activation circuit configured to apply current between the anode and cathode to deliver a drug by electrotransport when the device is in an on state and not in the off state; and
   wherein the device is configured to shut down when there is a current flowing between the anode and cathode that is greater than an Output Current Off threshold when the device is in an off state while powered on;
   further wherein the device is configured to automatically and periodically determine if there is a current flowing between the anode and cathode when the activation circuit is in the off state while powered on.

2. The device of claim 1, wherein the device is configured to determine if there is a potential difference between the anode and the cathode when the activation circuit is in the off state while powered on.

3. The device of claim 1, further configured to determine if there is a change in capacitance between the anode and cathode when the activation circuit is in the off state while powered on.

4. The device of claim 1, further configured to determine if there is a change in inductance between the anode and cathode when the activation circuit is in the off state while powered on.

5. The device of claim 1, further comprising a sensing circuit that independently determines an anode voltage and a cathode voltage and compares the potential difference between the anode voltage and cathode voltage to a threshold value.

6. The device of claim 5, further including a switch connected between a reference voltage source and a sense resistor, further comprising an off-current module configured to close the switch periodically to determine the potential difference between the anode voltage and cathode voltage.

7. The device of claim 1, further configured to determine if there is a current flowing between the anode and cathode when the activation circuit is in the off state at least once per minute.

8. The device of claim 1, further configured to determine if there is a current flowing between the anode and cathode when the activation circuit is in the off state between at least once every 10 ms and once every 10 minutes.

9. The device of claim 1, further configured to wait at least 10 ms before determining if there is a current flowing between the anode and cathode when the activation circuit is in the off state.

10. The device of claim 1, wherein the device has a two-part structure comprising:
    an electrical module including the activation circuit and an off-current module; and
    a reservoir module including the anode and the cathode and a source of drug to be delivered, wherein the drug comprises fentanyl;
    wherein the electrical module and reservoir module are configured to be combined prior to application to a patient.

11. The device of claim 1, further configured to indicate that there is a current flowing between the anode and cathode when the activation circuit is in the off state while powered on where the current flowing is above the Output Current Off Threshold.

12. The device of claim 1, wherein the Output Current Off Threshold is about 9 µA.

13. The device of claim 1, further comprising an Rsense resistor and an Rsense accuracy module configured to verify the accuracy of an Rsense resistance value.

14. The device of claim 1, further comprising an anode/cathode voltage difference test that measures the anode voltage and the cathode voltage using the ADC and calculates the voltage difference between the two.

15. The device of claim 1, further comprising a reservoir module including the anode and the cathode and a source of the drug to be delivered, wherein the drug comprises fentanyl.

16. A method of automatically and periodically confirming that drug will not be delivered by an electrotransport drug delivery device when the device is in an off state while powered on, the method comprising:
    determining if there is a current flowing between an anode and a cathode of the electrotransport drug delivery device when the electrotransport drug delivery device is in an off state while powered on, wherein the electrotransport drug delivery device includes an activation circuit that is configured to apply current between the anode and the cathode to deliver a drug when the device is in an on state and not deliver drug in the off state; and
    triggering an indicator to indicate a leak current if there is a current flowing between the anode and cathode that is greater than an Output Current Off Threshold when the electrotransport drug delivery device is in an off state while powered on, wherein triggering an indicator comprises one or more of: a visible notification, an audible notification, and a vibratory notification; and
    performing a device shutdown when the indicator is triggered.

17. The method of claim 16, further comprising repeating the determining step periodically while the activation circuit is in an off state.

18. The method of claim 16, further comprising repeating the determining step at least once every 10 minutes while the activation circuit is in an off state and the device is powered on.

19. The method of claim 16, wherein the Output Current Off Threshold is about 9 µA.

20. The method of claim 16, wherein determining if there is a current flowing between the anode and cathode of the electrotransport drug delivery device comprises independently determining an anode voltage and a cathode voltage and comparing the potential difference between the anode voltage and cathode voltage to the threshold value.

21. The method of claim 16, wherein determining if there is a current flowing between the anode and cathode of the electrotransport drug delivery device comprises independently connecting a reference voltage source and a sense resistor with each of the anode and cathode to determine the potential difference between the anode voltage and cathode voltage.

22. The method of claim 16, wherein triggering the indicator comprises illuminating a light and/or sounding an alarm on the device.

23. The method of claim 16, wherein determining comprises determining if there is current flowing between the anode and the cathode of the electrotransport drug delivery device when the electrotransport drug delivery device is in the off state while powered on, wherein the electrotransport drug delivery device includes an activation circuit that is configured to apply current between the anode and the cathode to deliver fentanyl when the device is in the on state and not deliver drug in the off state.

* * * * *